(12) United States Patent
Bachhav et al.

(10) Patent No.: US 11,213,516 B2
(45) Date of Patent: Jan. 4, 2022

(54) INTRAVAGINALLY APPLICABLE DEVICES COMPRISING ANTIVIRAL COMPOUNDS

(71) Applicant: AICURIS ANTI-INFECTIVE CURES GMBH, Wuppertal (DE)

(72) Inventors: Yogeshwar Bachhav, Mumbai (IN); Susanne Bonsmann, Cologne (DE); Tamara Pfaff, Dusseldorf (DE); Alexander Birkmann, Wuppertal (DE); Karl Malcolm, Belfast (IE)

(73) Assignee: AICURIS GMBH & CO. KG, Wuppertal (DE)

( * ) Notice: Subject to any disclaimer, the term of this patent is extended or adjusted under 35 U.S.C. 154(b) by 0 days.

(21) Appl. No.: 16/627,050

(22) PCT Filed: Jun. 28, 2018

(86) PCT No.: PCT/EP2018/067457
§ 371 (c)(1),
(2) Date: Dec. 27, 2019

(87) PCT Pub. No.: WO2019/002486
PCT Pub. Date: Jan. 3, 2019

(65) Prior Publication Data
US 2020/0121664 A1    Apr. 23, 2020

(30) Foreign Application Priority Data
Jun. 28, 2017   (EP) .................................... 17178439

(51) Int. Cl.
*A61K 31/4436*   (2006.01)
*A61P 31/22*   (2006.01)
*A61K 9/00*   (2006.01)

(52) U.S. Cl.
CPC ........ *A61K 31/4436* (2013.01); *A61K 9/0036* (2013.01); *A61P 31/22* (2018.01)

(58) Field of Classification Search
CPC ........ A61K 31/4436; A61K 9/00; A61P 31/22
See application file for complete search history.

(56) References Cited

U.S. PATENT DOCUMENTS

| | | | |
|---|---|---|---|
| 10,137,117 B2 | 11/2018 | Schwab et al. | |
| 2008/0069850 A1 | 3/2008 | Shalaby et al. | |
| 2014/0209100 A1 | 7/2014 | Kiser et al. | |
| 2014/0221433 A1* | 8/2014 | Schwab .................. | A61P 31/22 514/342 |
| 2016/0000797 A1* | 1/2016 | Checcone ............... | A61P 31/18 424/432 |

FOREIGN PATENT DOCUMENTS

| | | |
|---|---|---|
| EP | 2573086 A1 | 3/2013 |
| WO | 13013172 A1 | 1/2013 |

OTHER PUBLICATIONS

Clinical Trial Protocol May 2, 2013.*
BOG Science (2010).*
MedKoo (2019).*
International Search Report PCT/EP2018/067457 dated Sep. 19, 2018 (pp. 1-2).

* cited by examiner

*Primary Examiner* — Shirley V Gembeh
(74) *Attorney, Agent, or Firm* — Millen, White, Zelano & Branigan, PC; Ryan Pool

(57) ABSTRACT

The present invention relates to field of intravaginally applicable devices that release antiviral compounds. In particular, the present invention relates to vaginal rings comprising a matrix releasing at least one antivirally active compound, in particular anti-herpetic compound N-[5-(aminosulfonyl)-4-methyl-1,3-thiazol-2-yl]-N-methyl-2-[4-(2-pyridinyl)-phenyl]-acetamide (in the following also referred to as "Pritelivir") or salts thereof. The present invention therefore relates to the treatment and prevention of herpes infections.

19 Claims, 10 Drawing Sheets

A: daily release ± SD vs time
B: cumulatice release vs time
C: cumulative release vs root time Data points in A represent mean ± SD (n=4)
Data points in B and C represent mean values only (n=4)

d: day(s), LLOQ: lower limit of quantification d: day(s), LLOQ: lower limit of quantification d: day(s), VF: vaginal fluid d: day(s), VF=vaginal fluid EC$_{50}$: 50% effective concentration

INTRAVAGINALLY APPLICABLE DEVICES COMPRISING ANTIVIRAL COMPOUNDS

The present invention relates to intravaginal devices that release antiviral compounds. In particular, the present invention relates to intravaginal ring devices for vaginal administration of at least one antiviral drug substance, including the anti-herpetic compound N45-(aminosul-fonyl)-4-methyl-1,3-thiazol-2-yl]-1-N-methyl-2-[4-(2-pyridinyl)-phenyl]-acetamide (in the following also referred to as "Pritelivir") or salts thereof. The present invention therefore relates to the treatment and prevention of herpes infections.

BACKGROUND

Herpes simplex viruses (HSV) frequently cause infections of various organs in humans, e.g. skin, mouth, throat, eyes, central nervous system and the anogenital region. HSV can be distinguished into two types, HSV Type 1 (HSV-1) and HSV Type 2 (HSV-2). While HSV-1 primarily infects skin, mouth, throat, eye, central nervous system, HSV-2 is primarily responsible for anogenital infections. However, both types of HSV may infect any of the above organs.

HSV-1 and/or HSV-2 infections are the cause of diseases such as labial herpes (cold sores mainly due to infections with HSV-1), genital herpes (mainly due to HSV-2 infections), but may rarely also cause severe diseases such as keratitis and encephalitis. The viruses are ubiquitously distributed throughout the world. A well-known drug used in the treatment of herpes simplex infections is acyclovir (2-Amino-1,9-dihydro-9-((2-hydroxyethoxy)methyl)-6H-purin-6-one), which is a specific inhibitor of the viral deoxyribonucleic acid (DNA) polymerase.

Anogenital infections generally arise due to sexual intercourse. Men are less frequently infected than women. Condoms provide protection against HSV-infections. Unprotected sexual intercourse without condoms thus represents an opportunity for the virus to spread to previously non-infected individuals. Further, in particular, vaginal herpes infections represent a rare but serious risk for post partum infections of newborns. The vagina is an important application site for drug delivery, especially for local therapy of different diseases, such as bacterial, fungal and protozoan infections, for human immunodeficiency virus (HIV) prevention, delivery of contraceptives, spermicides or labor-inducers and for the treatment of precancerous lesions [Pereira R. R., Bruschi M. L., Vaginal mucoadhesive drug delivery systems, Drug Dev. Ind. Pharm. 2012; 38:643-652; Hussain A., Ahsan F., The vagina as a route for systemic drug delivery, J. Control. Release, 2005; 103:301-313; Valenta C., The use of mucoadhesive polymers in vaginal delivery. Adv. Drug Deliv. Rev. 2005; 57: 1692-1712]. It may also serve an alternative route for systemic drug delivery [Owen D. H., Katz D. F., A vaginal fluid simulant. Contraception 1999; 59:91-95]. It is a challenge to provide intravaginal devices that are simultaneously non-irritating, biocompatible and biostable and that ensure the release of effective amounts of active ingredients. These ingredients should not be released at an excessive rate, but should be suitable to provide an effective dose of the respective active ingredient over the desired treatment period of the patient in need thereof. WO2014/113693 A1 discloses modified release osmotic pumps for pH-responsive intravaginal drug delivery, and mentions in long lists that HSV infections may be treated using, e.g., acyclovir, and other antiviral drugs. There is, however, a need to provide new and effective means and methods for treating and preventing herpes infections, in particular, HSV infections of the genital tract.

The present invention addresses the above objectives and provides intravaginal devices for the administration of Pritelivir as well as methods of using the same. Pritelivir is an experimental antiviral compound useful in the treatment of HSV (Type 1 and Type 2, respectively) as disclosed in WO2006103011A1. It represents the first in a new class of antiviral agents that inhibit HSV replication by targeting the viral helicase-primase enzyme complex. Unlike the more conventional nucleoside analogues used for treatment of genital HSV-2 infections, such as acyclovir, Pritelivir does not require activation by phosphorylation and it is active in uninfected cells. Pritelivir exhibits potent in vitro activity against HSV-1 and HSV-2 isolates, including strains resistant to nucleoside analogues, and has shown efficacy in studies in animals, including a study of genital infection in guinea pigs. Pritelivir has also been reported to reduce the rates of genital HSV shedding and days with lesions in a dose-dependent manner in otherwise healthy men and women with genital herpes [Wald, A., et al., Effect of Pritelivir Compared With Valacyclovir on Genital HSV-2 Shedding in Patients With Frequent Recurrences: A Randomized Clinical Trial. JAMA, 2016. 316(23): p. 2495-2503; Wald, A., et al., Helicase-primase inhibitor pritelivir for HSV-2 infection. N Engl J Med, 2014. 370(3): p. 201-10].

DETAILED DESCRIPTION OF THE INVENTION

Figure 1:
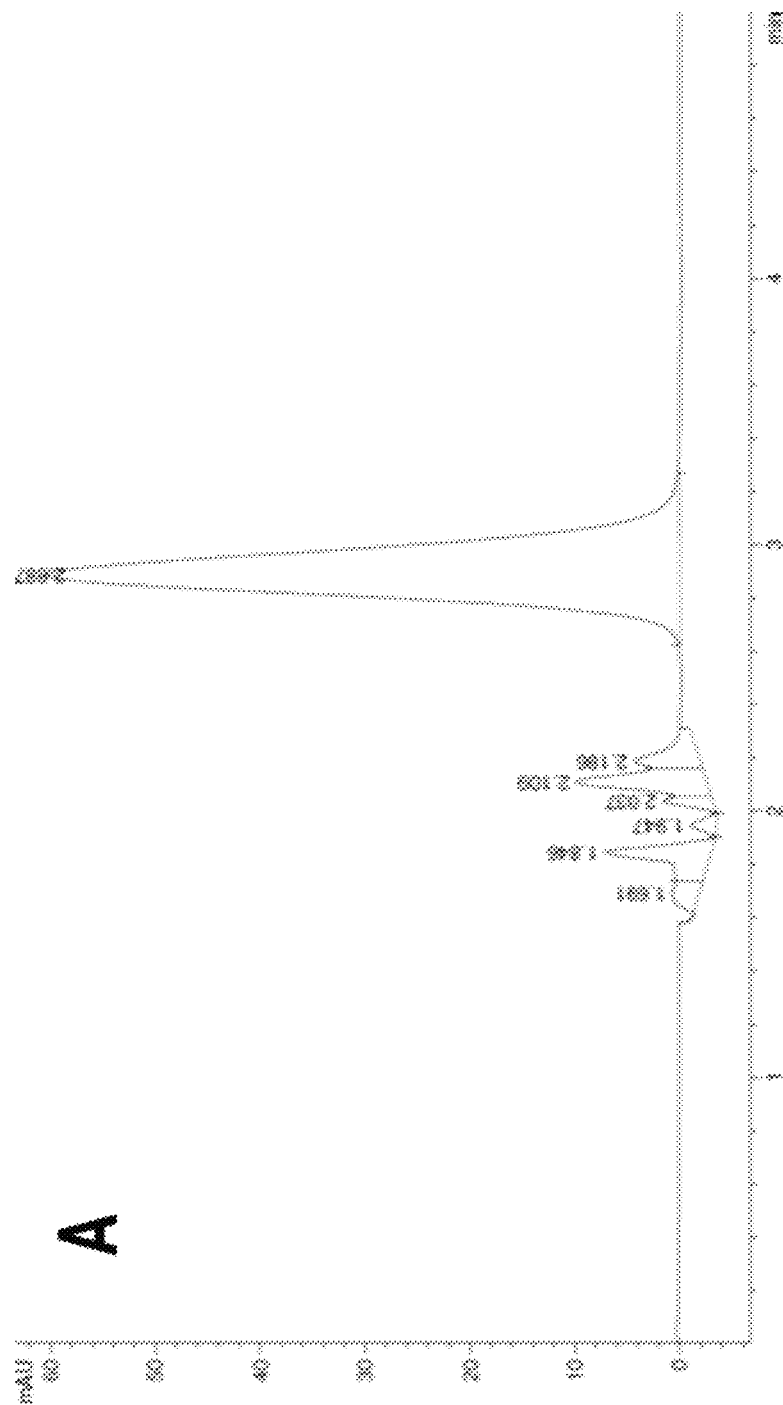
FIG. 1: Representative HPLC chromatograms for 8 μg/mL solutions of the Pritelivir free base (A) and Pritelivir mesylate salt (B) with the largest peaks at 2.887 min (FIG. 1(A) and at 2.884 min in FIG. 1B) in 1:1 isopropanol/$H_2O$ mixture.
Figure 1:
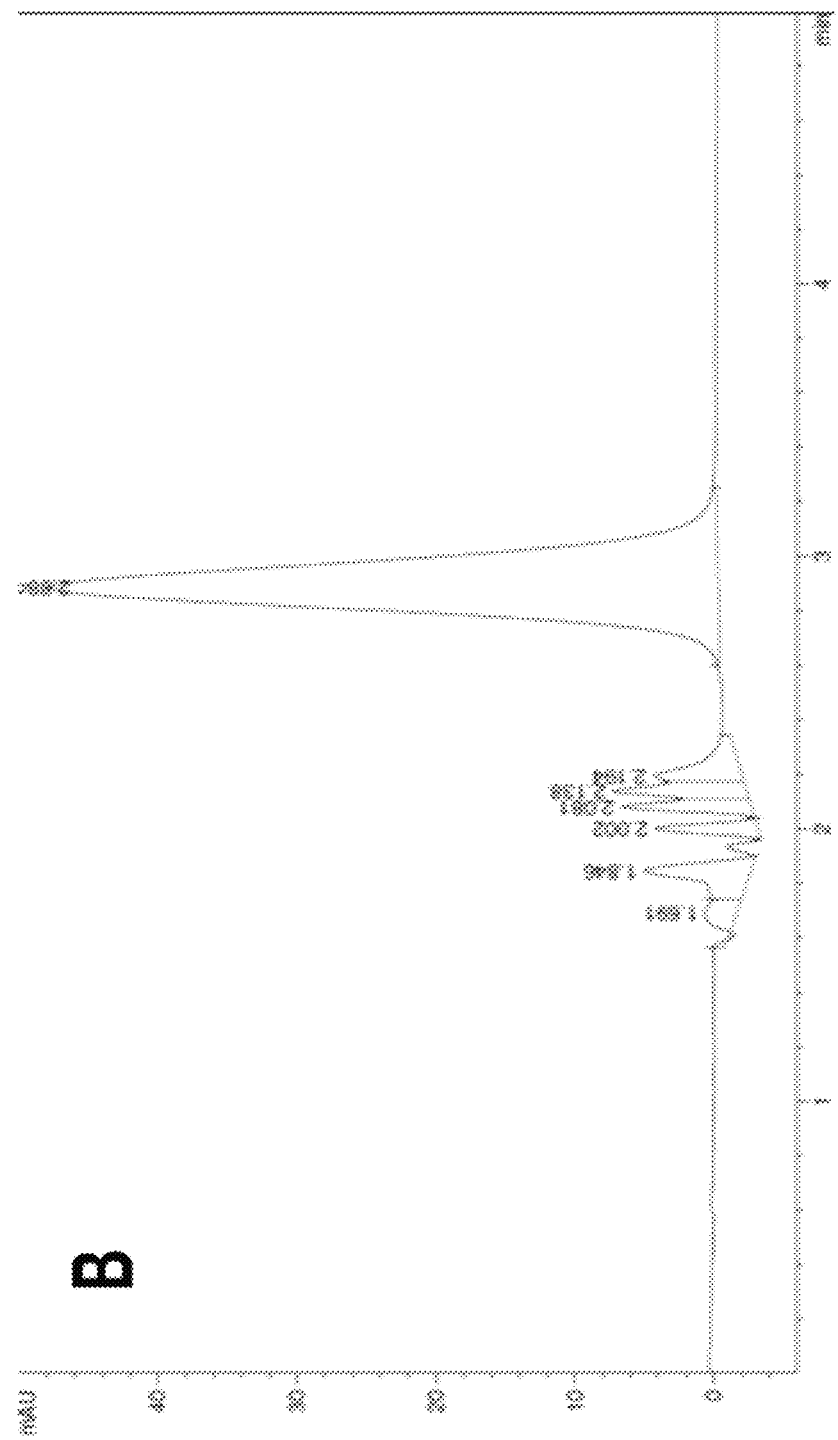

Before describing the invention in detail, it is deemed expedient to provide definitions for certain technical terms used throughout the description. Although the present invention will be described with respect to particular embodiments, this description is not to be construed in a limiting sense. Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

According to the present invention, the term "antivirally effective amount" means the total amount of each active component that is sufficient to show a meaningful patient benefit, i.e., healing of acute conditions characterized by inhibition of the herpes virus infection. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat, treating, treatment" as used herein and in the claims means preventing or ameliorating diseases associated with herpes virus infection. The terms "prophylaxis or prevention" as used herein and in the claims refers to the administration or use of the herein disclosed compounds or compositions in order to protect a non-infected organism or a non-infected cell of an organism from being infected, i.e., an organism may be infected by a virus, but the spread of the virus within the organism (from cell to cell) or within the organisms' social environment is prevented. The organism may be a human or other mammal. In one aspect of the invention, the organism to whom the compound or pharmaceutical composition is administered is a human being that is infected by a herpes virus, e.g., HSV-1 and/or HSV-2, or a human being that is in danger of being infected by such viruses.

In the context of the invention, the term immediate release refers to the drug release kinetic from the ring device when a significant amount of the drug is released within the first 24 h after administration. In the context of the invention, a burst release typically refers to an immediate release of the drug from the device.

In the context of the invention, the term sustained release refers to the drug release kinetic from the ring device when the drug is constantly released from the ring device over several days or weeks or months.

In the context of the invention, the term controlled release refers to the drug release kinetic from the ring device when the drug release depends on the characteristics of the device, e.g. type of polymer.

The physical and chemical characterization of the Pritelivir free base and the mesylate salt referred to herein was performed using compendial methods as per European Pharmacopoeia (Ph. Eur.) and/or the U.S. Pharmacopeial Convention (USP).

According to the present invention, a matrix type ring refers to a ring device made of a polymer matrix wherein the drug is physically and/or molecularly dispersed. The typical release kinetic is driven by the dissolution and diffusion mechanisms.

Herein below, various embodiments of the invention are explained in more detail. Wherever, respective alternatives in terms of ingredients in compositions, types of pharmaceutical compositions, concentrations of ingredients, periods of time of administration, frequencies of administration, medical indications to be treated are mentioned, the person skilled in the art would immediately understand that individual combinations can be made as long as these are technically possible or if not otherwise explicitly indicated.

The free base form of Pritelivir is shown in Formula (I):

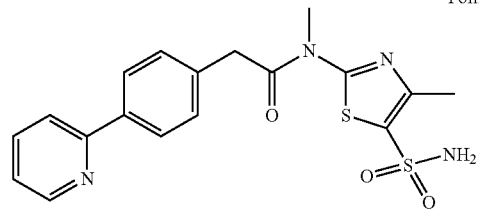

Formula (I)

The term(s) "prophylaxis and/or prevention" or similar term(s) in the art pertinent to the instant invention clearly mean to one of ordinary skill in the art the suppression or reduction of the recurrence of infection or the suppression or reduction of transmission of infection with HSV-1 or HSV-2. In the context of the invention, the term(s) "prophylaxis and/or prevention" does not mean with, even under the broadest reasonable interpretation, the complete and total absence of any infectious virus particles or infected cells from a patient. With the background of the instant invention, such a position is reasonable in the art pertinent to the disclosed subject matter. In support of these definitions of the term(s) "prophylaxis and/or prevention" the following publications are herein incorporated by reference:

Abdool Karim, S. S., et al. (2015). Tenofovir Gel for the Prevention of Herpes Simplex Virus Type 2 Infection. N Engl. J Med 373, 530-539.

Andrei, G. et al (2011). Topical tenofovir, a microbicide effective against HIV, inhibits herpes simplex virus-2 replication. Cell Host. Microbe 10, 379-389.

Corey, L., et al., (2004). Once-daily valacyclovir to reduce the risk of transmission of genital herpes. N. Engl. J. Med. 350, 11-20.

Gold, D., and Corey, L., MINIREVIEW Acyclovir Prophylaxis for Herpes Simplex Virus Infection. Antimicrobial Agents and Chemotherapy, March 1987, p. 361-367.

Kleymann, G., et al. (2002). New helicase-primase inhibitors as drug candidates for the treatment of herpes simplex disease. Nat. Med. 8, 392-398.

Mertz, G. J., et al., (1985). Frequency of acquisition of first-episode genital infection with herpes simplex virus from symptomatic and asymptomatic source contacts. Sex Transm. Dis. 12, 33-39.

Reitano, M., et al., (1998). Valaciclovir for the suppression of recurrent genital herpes simplex virus infection: a large-scale dose range-finding study. International Valaciclovir HSV Study Group. J. Infect. Dis. 178, 603-610.

Schiffer, J. T., et al., (1997). Frequent genital herpes simplex virus 2 shedding in immunocompetent women. Effect of acyclovir treatment. J. Clin Invest 99, 1092-1097.

Tyring, S., Baker, D., Snowden, W., Valacyclovir for Herpes Simplex Virus Infection: Long-Term Safety and Sustained Efficacy after 20 Years' Experience with Acyclovir. The Journal of Infectious Diseases 2002; 186(Suppl 1):S40-6.

Wald, A., et al. (2014). Helicase-primase inhibitor Pritelivir for HSV-2 infection. N Engl. J Med 370, 201-210.

Wald, A., et al. (2016). Effect of Pritelivir Compared With Valacyclovir on Genital HSV-2 Shedding in Patients With Frequent Recurrences: A Randomized Clinical Trial. JAMA 316(23):2495-2503. Erratum in: JAMA. 2017 Feb. 14; 317 (6):648.

Wald, A., et al. (2000). Reactivation of genital herpes simplex virus type 2 infection in asymptomatic seropositive persons. N. Engl. J. Med. 342, 844-850.

Zhu, J., et al. (2007). Virus-specific CD8+ T cells accumulate near sensory nerve endings in genital skin during subclinical HSV-2 reactivation. J. Exp. Med. 204, 595-603.

These documents support the correlation between helicase-primase inhibition and the prevention or prevention of transmission of HSV infection as having been demonstrated in the art. Further, the above mentioned Kleymann, 2002, teaches on page 396, bottom of the left column, that recurrent disease and asymptomatic virus shedding are nearly completely suppressed by helicase-primase inhibitors, which should decrease person-to-person transmission, i.e., to effectively prevent the transmission of HSV. The above mentioned disclosure in Corey, 2004, teaches at the bottom of page 11 and on page 17, first column, that once daily suppressive therapy with valacyclovir significantly reduces the risk of transmission, i.e., prevented the transmission, of genital herpes among heterosexual, HSV-2 discordant couples. The study achieved these results with a drug that has been shown to suppress shedding of HSV type 2 (HSV-2) on genital mucosal surfaces. Further, it has been found that the frequency and amount of HSV that is shed subclinically on genital mucosal surfaces is the principal source of transmitted infections. As such, an approach to reduce the frequency and amount of HSV that is shed subclinically on genital mucosal surfaces is a way to achieve prevention of transmission of herpes.

Karim, 2015, teaches at the bottom of page 530 that pericoital application of tenofovir gel reduced HSV-2 acquisition in women, i.e., prevented HSV acquisition. The effectiveness was a reduction of 51% (page 534, second column) In an earlier study by the same group dating back to 2010 (see citation 6 in this reference), it was shown that pericoital application of a topical vaginal-gel formulation of tenofovir reduced HIV acquisition. While HIV is a different virus, and in view of the above, it will not be surprising to those of ordinary skill in the art that a drug is able to prevent the acquisition of a viral infection. Moreover, such is explicitly confirmed to occur by Karim in the case of HSV. Gold and Corey from March 1987 support the well-known effective prophylaxis of acyclovir (i.e., viral DNA polymerase inhibitor). In addition, Tyring et al. from 2002 supports the efficacy of the prodrug valacyclovir (i.e., viral DNA polymerase inhibitor).

The person skilled in the art is aware that for HSV-1 and HSV-2 infections, although the viruses are present within the body due to infection, there is no symptomatic outbreak because Pritelivir effectively suppresses viral shedding and outbreak, which is "prophylaxis" or "suppression" against the resultant symptoms of HSV-1 and HSV-2 infection. In further support of the prophylaxis=suppression aspect of the invention, the above mentioned citations for valacyclovir (i.e. Tyring et al. 2002) and acyclovir (i.e. Gold et al. 1987) are reiterated, which also prove that it is well established that HSV infections are asymptomatic in normal individuals, and what prophylactic/suppressive therapy means in this art. Moreover, effective HSV-prophylaxis has been clinically demonstrated in human trials (Wald et al., 2014 and 2016, supra). Finally, it is known that the helicase-primase inhibitor Pritelivir has an even higher antiviral efficacy against HSV than tenofovir has and thus, for the skilled person, Pritelivir also would be expected to have a more pronounced prophylactic efficacy. In this regard, particularly relevant are the publications by Andrei et al. and Kleymann et al. as mentioned above. The $IC_{50}$-values demonstrated therein for tenofovir are significantly higher than those of Pritelivir.

As used herein, the term "anti-inflammatory agent" refers generally to any compound or combination of compounds that, upon administration to an individual experiencing inflammation, tends to reduce such inflammation, e.g. steroids, and non-steroidal anti-inflammatory drugs (NSAIDs).

As used herein "centrally and peripherally acting analgesics" comprise opioid analgesics. Opioid analgesics comprise, e.g. buprenorphine or a physiologically acceptable salt or ester thereof, suitable opioid analgesics include alfentanil, allylprodine, alphaprodine, anileridine, benzylmorphine, bezitramide, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalbuphine, nalorphine, naloxone, naltrexone, normorphine, norpipanone, opium, oxycodone, oxymorphone, papaveretum, pentazocine, phenadoxone, phenomorphan, phenazocine, phenoperidine, piminodine, piritramide, profadol, propheptazine, promedol, properidine, propiram, propoxyphene, sufentanil, tilidine and tramadol. Also included are esters, salts and mixtures of any of the foregoing.

As used herein, non-opioid analgesics comprise, e.g., NSAID, a tricyclic antidepressant (e.g. amitryptyline), an anticonvulsant (e.g. gabapentin) or an antimigraine compound (e.g. sumatriptan or naratriptan). The NSAID may be a cyclooxygenase (COX) COX-1 or COX-2 inhibitor. Specific examples of NSAIDs include ibuprofen, flurbiprofen, diclofenac, indomethacin, piroxicam, ketoprofen, etodolac, diflusinal, meloxicam, aceclofenac, fenoprofen, naproxen, tiaprofenic acid, tolmetin, celecoxib and rofecoxib, and their physiologically acceptable salts and esters. Suitable salts are alkali addition salts such as the potassium or sodium salt.

In the compositions of the invention, long and short acting local and volatile anesthetics may be used that are selected from the group comprising bupivacaine, lidocaine, xyclocaine, tetrodotoxin (TTX), saxitoxin (STX), etc.

In one embodiment a pharmaceutical composition obtainable by formulating Pritelivir may further comprise a local anesthetic.

In one embodiment a pharmaceutical composition obtainable by formulating Pritelivir comprises the local anesthetic lidocaine.

In another embodiment the present application relates to the pharmaceutical composition as defined in any one of the preceding embodiments, further comprising or that is formulated to initially comprise an active compound selected from the group comprising anti-inflammatory agents, antiviral agents, centrally and peripherally acting analgesics, (local) anesthetics.

The combination of Pritelivir free base or the mesylate salt thereof and a further active agent like an anti-inflammatory, immunomodulatory, or antiviral agent, such as therapeutic vaccines, siRNAs, antisense oligonucleotides, nanoparticles or virus-uptake inhibitors such as n-docosanol, may be administered using the herein disclosed devices.

In one embodiment, the invention relates to a device for the intravaginal administration of Pritelivir, or a salt, a solvate, or a polymorph thereof.

In another embodiment, the invention relates to the device according to the preceding embodiment, wherein Pritelivir is selected from the group comprising the Pritelivir free base and Pritelivir mesylate salt.

In another embodiment, the invention relates to the device according to the preceding embodiments, comprising a composition comprising the Pritelivir free base and the Pritelivir mesylate salt.

In another embodiment, the invention relates to the device according to the preceding embodiments, wherein the Pritelivir comprises the Pritelivir free base and/or Pritelivir mesylate salt. It is possible to use any solid states of Pritelivir, e.g. amorphous forms or crystalline forms, in any of the previous and following embodiments, except in cases where this is explicitly excluded.

In another embodiment, the invention relates to the device according to the preceding embodiments, wherein the device comprises a biostable and biocompatible polymer matrix.

In another embodiment, the invention relates to the device according to the preceding embodiments, wherein the device comprises a biostable and biocompatible polymer matrix comprising a silicone elastomer, but other materials such as thermoplastic materials may also be used as known in the art, e.g. polyurethane (PU), polyethylene (PE), polypropylene (PP), ethylene vinyl acetate (EVA).

In another embodiment, the invention relates to the device according to the preceding embodiments, wherein the device comprises a biostable and biocompatible polymer matrix comprising a thermoplastic polymer.

In another embodiment, the invention relates to the device according to the preceding embodiments, wherein the device is an intravaginal ring. In another embodiment, the invention relates to the device according to the preceding embodiments is a microtablet, wherein said microtablet may be coated or uncoated. Microtablets are known in the art and may comprise ingredients that are per se known in the art, e.g. solubilizing agents, stabilizers, gelling agents, diluents, disintegrants, coating agents, dispersing agents and the like.

In another embodiment, the invention relates to the intravaginal ring wherein the intravaginal ring is a matrix type ring where the drug is physically and/or molecularly dispersed within the matrix.

In another embodiment, the invention relates to the intravaginal ring wherein the intravaginal ring is reservoir type ring, or a sandwich/shell type ring, or a multiple partial core type ring, or an insertable core type ring, or an over-molded metal spring ring or any other ring type known.

In another embodiment, the invention relates to the device according to the preceding embodiments, wherein the device is suitable for immediate release of Pritelivir.

In another embodiment, the invention relates to the device according to the preceding embodiments, wherein the device is suitable for sustained release of Pritelivir.

In another embodiment, the invention relates to the device according to the preceding embodiments, wherein the device is suitable for controlled release of Pritelivir.

In another embodiment, the invention relates to the device according to the preceding embodiments, wherein the device is suitable for immediate and sustained release of Pritelivir.

In another embodiment, the invention relates to the device according to the preceding embodiments, wherein the device is suitable for immediate and controlled sustained release of Pritelivir.

In another embodiment, the invention relates to the device according to the preceding embodiments, wherein the device comprises Pritelivir in a total amount of at least 25 mg, at least 30 mg, at least 40 mg, at least 50 mg, at least 75 mg, at least 100 mg, at least 150 mg, at least 200 mg, at least 225 mg, at least 230 mg, or at least 240 mg.

In another embodiment, the invention relates to the device according to the preceding embodiments, wherein the device is suitable for immediate release of Pritelivir, and wherein the 50% anti-HSV effective concentration ($EC_{50}$) of ≥0.03 µM is measured after at least 30 minutes, or after at least 60 minutes, to at least 24 hours in vaginal fluid post-administration of the device.

In another embodiment, the invention relates to the device according to the preceding embodiments, wherein the device is suitable for immediate and sustained release of Pritelivir, and wherein the anti-HSV $EC_{50}$ of ≥0.03 µM is measured at least for 7 days post-administration of the device in vaginal fluid and/or vaginal and/or vulvar tissue.

In another embodiment, the invention relates to the device according to the preceding embodiments, wherein the device is suitable for immediate and sustained release of Pritelivir, and wherein the anti-HSV $EC_{50}$ of ≥0.03 μM is measured at least for 14 days post-administration of the device in vaginal fluid and/or vaginal and/or vulvar tissue.

In another embodiment, the invention relates to the device according to the preceding embodiments, wherein the device is suitable for immediate and sustained release of Pritelivir, and wherein the anti-HSV $EC_{50}$ of ≥0.03 μM is measured at least for 21 days post-administration of the device in vaginal fluid and/or vaginal and/or vulvar tissue.

In another embodiment, the invention relates to the device according to the preceding embodiments, wherein the device is suitable for immediate and sustained release of Pritelivir, and wherein the anti-HSV $EC_{50}$ of ≥0.03 μM is measured at least for 28 days post-administration of the device in vaginal fluid and/or vaginal and/or vulvar tissue.

In another embodiment, the invention relates to the device according to the preceding embodiments, wherein the device comprises Pritelivir in an amount selected from the group of ranges comprising 0.01% w/w to 40.0% w/w, 0.1% w/w to 20.0% w/w, 0.25% w/w-10.0% w/w, 0.25% w/w to 7.5% w/w, and 0.25% w/w to 1.0% w/w.

In another embodiment, the invention relates to the device according to the preceding embodiments, wherein the device comprises Pritelivir in an amount selected from the range of 0.3 to 5.5% w/w, e.g. 0.3 to 5.25% w/w.

In another embodiment, the invention relates to the device according to the preceding embodiments, wherein the concentration of Pritelivir in a plasma sample of an individual receiving said device in a period of 1 to 28 days post-administration of said device is ≤100 nM≤50 nM, ≤30 nM, ≤20 nM, or ≤10 nM. In one embodiment, the concentration of Pritelivir in a plasma sample of an individual receiving said device in a period of 1 to 28 days post-administration of said device is ≤100 nM. In one embodiment, the concentration of Pritelivir in a plasma sample of an individual receiving said device in a period of 1 to 28 days post-administration of said device is ≤50 nM, In one embodiment, the concentration of Pritelivir in a plasma sample of an individual receiving said device in a period of 1 to 28 days post-administration of said device is ≤30 nM. In one embodiment, the concentration of Pritelivir in a plasma sample of an individual receiving said device in a period of 1 to 28 days post-administration of said device is ≤20 nM. In one embodiment, the concentration of Pritelivir in a plasma sample of an individual receiving said device in a period of 1 to 28 days post-administration of said device is ≤10 nM.

In another embodiment, the invention relates to the device according to the preceding embodiments, wherein the plasma concentration of Pritelivir in a period of 1 to 28 days post-administration of the device is ≤50 nM, ≤30 nM, ≤20 nM, or ≤10 nM. In one embodiment, the plasma concentration of Pritelivir in a period of 1 to 28 days post-administration of the device is ≤50 nM. In one embodiment, the plasma concentration of Pritelivir in a period of 1 to 28 days post-administration of the device is ≤30 nM. In one embodiment, the plasma concentration of Pritelivir in a period of 1 to 28 days post-administration of the device is ≤20 nM. In one embodiment, the plasma concentration of Pritelivir in a period of 1 to 28 days post-administration of the device is ≤10 nM.

In another embodiment, the invention relates to the device according to the preceding embodiments, wherein the concentration of Pritelivir in vaginal fluid or in vaginal or vulvar tissue in a period of 1 to 28 days, e.g. in a period of 1 to 14 days, post-administration of the device is in a range of 0.1 to 3,000 μM.

In another embodiment, the invention relates to the device according to the preceding embodiments, characterized in that a daily dose of 0.1 to 500.0 μg is released from the ring or the microtablet in a period from day 2 to day 14 post-administration of the device to a patient, and/or wherein a daily dose of 0.1 to 50.0 μg is released from the ring in a period from day 14 to day 28 post-administration of the device.

In another embodiment, the invention relates to the device according to the preceding embodiments, characterized in that a concentration of 0.001 to 750 μM of Pritelivir is present in vaginal tissue 28 days and/or about 2.0 to 250 μg Pritelivir per gram vaginal tissue post-administration of the device.

In another embodiment, the invention relates to the device according to the preceding embodiments, wherein said device comprises at least one additional active ingredient. In another embodiment, the invention relates to the device according to the preceding embodiments, wherein said device comprises at least one additional active ingredient, selected from the group of antiviral agents, anti-inflammatory agents, analgesics, anesthetics, antibiotics, hormones, and contraceptive agents. The hormones may be selected from the group comprising sex hormones and steroid hormones. The contraceptive agent(s) may be selected from the group comprising non-hormonal and hormonal contraceptives, e.g., steroidal substances for use in hormone replacement therapy such as progestational compounds (e.g., norethindrone acetate and NESTORONEM™ (i.e., 16-methylene-17α-acetoxy-19-norpregnene-3,20-dione)), and estrogenic substances (e.g., ethynylestradiol) and other steroidal compounds useful in hormone replacement regimens, progestin, estradiol, metal salts of 1,1,5,5-tetrasubtituted -dithiobiurets as spermiostatic agents, light metals such as sodium and potassium, alkaline earth metals such as calcium and barium, and heavy metals such as zinc, cadmium, tin, mercury, copper, nickel, chromium, iron, manganese, and cobalt, given orally as chelates, that have been shown to form dithiobiuret salts, which act as contraceptive and pregnancy terminators, benzylalkonium chloride, octoxynol-9, nonoxyl-9, ricinoleic acid, and phenol mercury acetates acting as spermicides, or other compounds such as progesterone, chlormadinone acetate, norethisterone acetate, cyproterone acetate, desogestrel, levenorgestrel, other natural and/or synthetic gestagens, antigestagens and hormonal analogs with gestagen or antigestagen action, as well as hormonal compounds which rapidly split off at least one gestagen following taking.

In another embodiment, the invention relates to the device according to the preceding embodiments, wherein said device comprises at least one additional antiviral active ingredient, wherein said ingredient is selected from the group comprising HSV antiviral agent, an HIV antiviral agent, or both HSV and HIV antiviral agents.

In another embodiment, the invention relates to the device according to the preceding embodiments, wherein said HSV antiviral agents are selected from a group comprising valacyclovir, acyclovir, famciclovir, ganciclovir, glycyrrhizic acid, *Sambucus nigra*, propolis, L-lysine, docosanol, valganciclovir, or a salt, solvate or a combination thereof.

In another embodiment, the invention relates to the device according to the preceding embodiments, wherein said HIV antiviral agents are selected from a group comprising dapivirine, tenofovir, darunavir, emtricitabine, lamivudine, efavirenz, raltegravir, dolutegravir, maraviroc, rilpirivine, or a salt, solvate or a combination thereof.

In another embodiment, the invention relates to the device according to the preceding embodiments, wherein the said device releases Pritelivir in vitro in an amount of 10.0 to 500.0 µg on day 1 and/or 10.0 to 125 µg after 14 days in a 1:1 Vol/Vol solution of isopropanol:$H_2O$, e.g., when determined by high performance liquid chromatography (HPLC). HPLC analysis may, for example, be conducted using an Agilent 1200 Series HPLC system, consisting of a quaternary HPLC pump, an auto sampler, an in-line Degasser AF Unit, a dual λ absorbance detector, and a column heater. A BDS Hypersil C18 (Thermo Scientific) column (length 150 mm, id 4.6 mm, particle size 3 µm) may be used. The mobile phase may comprise 45% of 1% w/v glacial acetic acid and 55% methanol pumped isocratically at a flow rate of 1 mL/min. The sample injection volume may be 25 µL, the column temperature 25° C., and detection may be performed at 280 nm. Run time for the method may be 5 min.

In another embodiment, the invention relates to the device according to the preceding embodiments, wherein said device releases Pritelivir in vitro at a rate of 0.1 to 500.0 µg/day in 1:1 Vol/Vol solution of isopropanol:$H_2O$, e.g., when determined by HPLC.

In another embodiment, the invention relates to the device according to the preceding embodiments for use in a method of treatment and/or prevention of a genital herpes virus infection. In another embodiment, the invention relates to the device according to the preceding embodiments for use in a method of treatment and/or prevention of a genital herpes virus transmission.

In another embodiment, the invention relates to the device according to the preceding embodiments, wherein the genital herpes virus is selected from the order of simplex viruses. In another embodiment, the invention relates to the device according to the preceding embodiments, wherein said simplex virus is selected from HSV-1 and HSV-2. In another embodiment, the invention relates to the device according to the preceding embodiments for use in a method of treatment and/or prevention of a genital herpes virus infection according to any one of the foregoing claims, wherein viral shedding and genital lesions and recurrences are suppressed.

In another embodiment, the invention relates to the device according to the preceding embodiments for use in a method of treatment and/or prevention of a genital herpes virus infection according to any one of the foregoing claims, wherein the device is for administration to patients in need thereof selected from the group of women diagnosed with a genital herpes virus infection, women who are HSV seropositive, women suspected to have a genital herpes virus infection, women suffering from or suspected to suffer from a bacterial or fungal infection of the genital tract or from a non-herpetic virus infection of the genital tract, women wishing to get pregnant, pregnant women, women having sexual intercourse with men diagnosed as suffering from or suspected to suffer from an infection of the genital tract, particularly an infection with HSV, women who are recipients of an organ transplant or expecting to receive an organ transplant, immunosuppressed women, women having sexual intercourse with men who are recipients of an organ transplant or expecting to receive an organ transplant, women having sexual intercourse with immunosuppressed men, women having children aged 0 to 18 years that are recipients of an organ transplant or expecting to receive an organ transplant or who are immunosuppressed, women suffering from an HIV or human papillomavirus (HPV) infection.

In another embodiment, the invention relates to the device according to the preceding embodiments for use in a method of treatment and/or prevention of a genital herpes virus infection according to any of the foregoing claims, wherein a first device is administered and replaced by at least one further device administered after 14 to 28 days, and wherein each subsequent device is administered after 14 to 28 days to replace the previously administered device.

In another embodiment, the invention relates to the device according to the preceding embodiments, wherein said device comprises at least two layers, wherein at least one exterior layer comprises a higher molar concentration of Pritelivir mesylate salt than the Pritelivir free base, and wherein at least one interior comprises a higher amount of the Pritelivir free base than Pritelivir mesylate salt.

In another embodiment, the invention relates to a medicinal kit comprising at least one device according to any of the preceding embodiments in a suitable container and instructions for use in a suitable packing.

In another embodiment, the invention relates to a process for the manufacture of a device according to any one of the preceding claims comprising the steps of:
  a) Mixing a biostable and biocompatible polymer and Pritelivir;
  b) Injection-molding or extruding the mixture obtained in step a). The molds may be preheated.

In another embodiment, the invention relates to a process for the manufacture of a device according to any one of the preceding claims comprising the steps of:
  a) Mixing a biostable and biocompatible thermoplastic material and Pritelivir;
  b) Injection-molding or extruding the mixture obtained in step a). The molds may be preheated.

In further embodiments, human-sized (for example, 56 mm od×7.6 mm id), matrix-type, silicone elastomer or thermoplastic material vaginal rings (or devices having other shapes) containing either 0.1 to 50 mg, e.g., 25 mg or 250-500 mg, e.g., 400 mg of Pritelivir can be manufactured by reaction injection molding of drug+silicone mixes. For example, Pritelivir can be weighed into a polypropylene Speedmixer container along with DDU-4320 silicone elastomer Part A (40 g) and Part B (40 g). After mixing, the mixture can be transferred to an injected into pre-heated custom, ring molds fitted to an injection molding machine. Subsequently, the cured rings can be removed from the molds.

In a further embodiment, the invention relates to a method of treatment or prevention/suppression of an infection with genital herpes caused by HSV-1 or HSV-2, or prevention/suppression of transmission of a genital herpes caused by HSV-1 or HSV-2, or prevention of acquisition of a genital herpes caused by HSV-1 or HSV-2, comprising administering to a subject in need thereof the device according to any of the preceding embodiments.

A further embodiment of the present invention is a method of treatment or suppression of the incidence of a HSV subtype 1 or 2 infection, or suppression of transmission of a HSV-1 or HSV-2 infection, comprising administering to a subject in need thereof a device according to the present invention providing an effective amount of Pritelivir free base or Pritelivir mesylate salt.

In a further embodiment, the invention relates to a medicinal kit comprising at least one device according to any of the preceding embodiments in a suitable container and instructions for use in a suitable packing.

Experiments

Preliminary studies to assess the potential for Pritelivir-releasing vaginal rings for free Pritelivir free base and Pritelivir mesylate salt have been conducted. Both Pritelivir free base and Pritelivir mesylate salt were successfully incorporated at 25 and 400 mg loadings into matrix-type vaginal rings manufactured from DDU-4320 medical grade, addition cure, silicone elastomer. No curing issues were observed and DSC analysis confirmed the presence of crystalline drug in the rings (both for Pritelivir free base and Pritelivir mesylate salt). In vitro release studies indicated that Pritelivir was released from the rings and it could be possible to achieve sustained release of Pritelivir using vaginal ring device.

HPLC Method for Quantification of Pritelivir

HPLC analysis was conducted using an Agilent 1200 Series HPLC system, consisting of a quaternary HPLC pump, an auto sampler, an in-line Degasser AF Unit, a dual λ absorbance detector, and a column heater. A BDS Hypersil C18 (Thermo Scientific) column (length 150 mm, id 4.6 mm, particle size 3 µm) was used. The mobile phase comprised 45% of 1% w/v glacial acetic acid and 55% methanol pumped isocratically at a flow rate of 1 mL/min. The sample injection volume was 25 µL, the column temperature was 25° C., and detection was performed at 280 nm. Run time for the method was 5 min Differential Scanning Calorimetry Analysis Differential scanning calorimetry (DSC) of Pritelivir in silicone elastomer samples was conducted using a DSCQ100 (TA Instruments) in standard heating ramp mode. Samples in aluminum pans were heated from room temperature to 300° C. at 10° C./min.

Thermogravimetric Analysis

Thermogravimetric analysis (TGA) of Pritelivir free base was conducted using a TGA Q200 instrument (TA Instruments) in standard heating ramp mode. Samples in aluminum pans were heated from room temperature to 300° C. at 10° C./min. All samples were investigated in triplicate.

Manufacture of Matrix-Type Silicone Elastomer Vaginal Rings

Human-sized (56 mm or ×7.6 mm id), matrix-type, silicone elastomer vaginal rings containing either 25 mg or 400 mg of Pritelivir were manufactured by reaction injection molding of drug+silicone mixes. For the 25 mg rings, 272 mg Pritelivir free base or Pritelivir mesylate salt was weighed into a polypropylene Speedmixer container along with DDU-4320 silicone elastomer Part A (40 g) and Part B (40 g). After mixing (Speedmixer DAK 150 FVZ-K; 3000 rpm for 30 sec), the mixture was transferred to a 60 mL disposable plastic syringe and injected into pre-heated (90° C.) custom, two-cavity ring molds fitted to a laboratory-scale injection molding machine. After 3 minutes, the cured rings were removed from the molds. For the 400 mg rings, 4325 mg of Pritelivir free base or Pritelivir mesylate salt was weighed. Four samples of each ring type were manufactured.

In Vitro Release Method

Pritelivir rings were individually placed into stoppered glass flasks containing 100 mL isopropanol/H₂O. The flasks were placed in a shaking orbital shaker (37° C., 60 rpm). The release medium was sampled (~5 mL) every 24 h over a fourteen day period, with complete replacement of the 100 mL release medium at each sampling point to maintain sink conditions. Quantification of Pritelivir free base or Pritelivir mesylate salt concentrations in the samples was performed using the HPLC-UV method.

HPLC Chromatograms

FIG. 1 shows a representative HPLC chromatograms for 8 µg/mL solutions of the free base of Pritelivir (A) and Pritelivir mesylate salt (B) in 1:1 isopropanol/H₂O mixture. The main peak of each chromatogram refers to Pritelivir free base (chromatogram A) and Pritelivir mesylate salt (chromatogram B), respectively. Characteristic peaks are shown with the largest peak in FIG. 1A at 2.887 min and the largest peak in FIG. 1B at 2.884.

DSC and TGA Data

Figure 2:
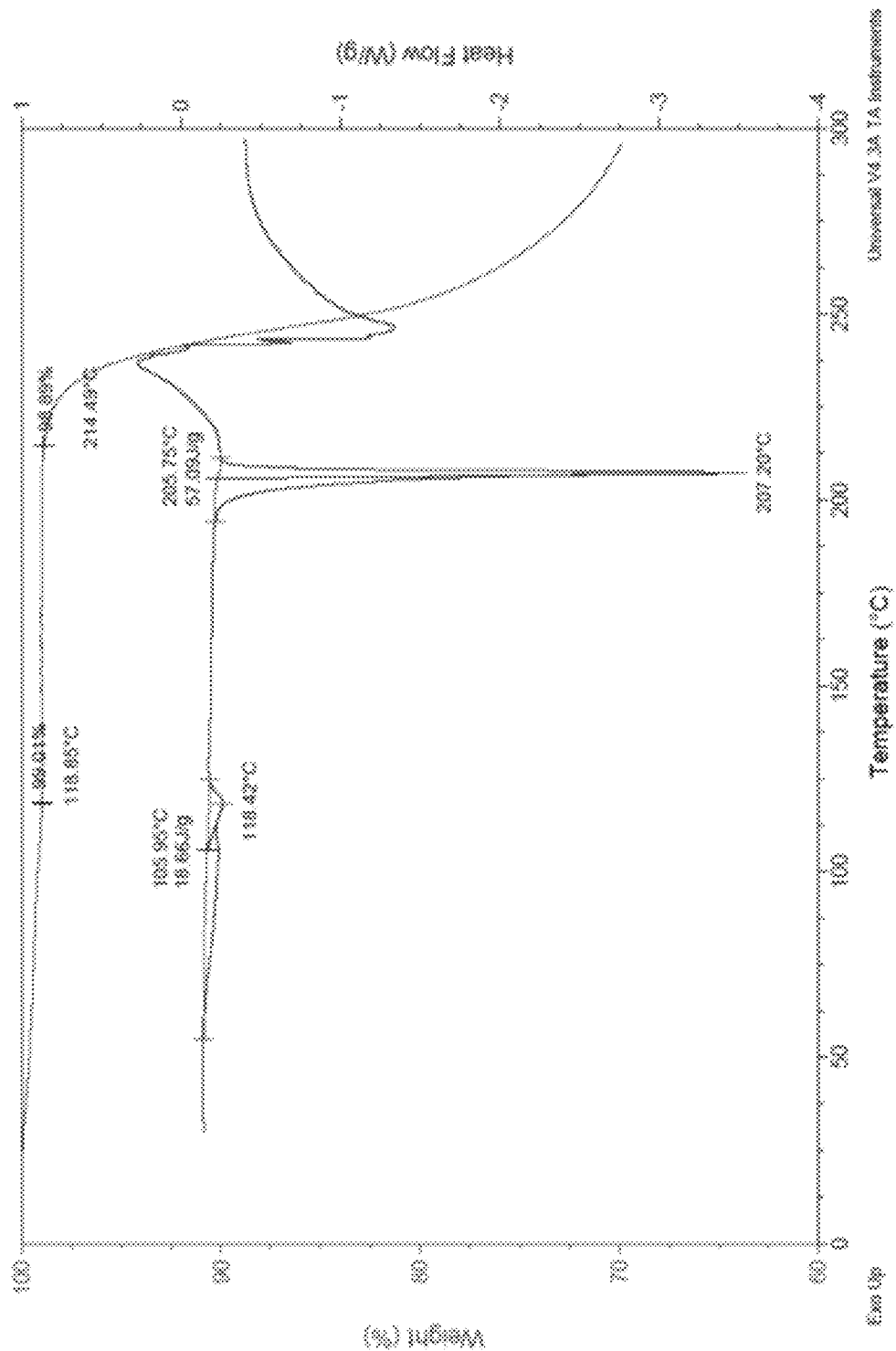
FIG. 2: Representative DSC (Differential Scanning Calorimetry) and TGA (Thermogravimetric analysis) of Pritelivir free base. Pritelivir shows two thermal transitions, a smaller one at 118° C. (attributed to loss of solvent of crystallization and/or a polymorphic transition) and the main crystalline melt at 206° C.
Figure 3:
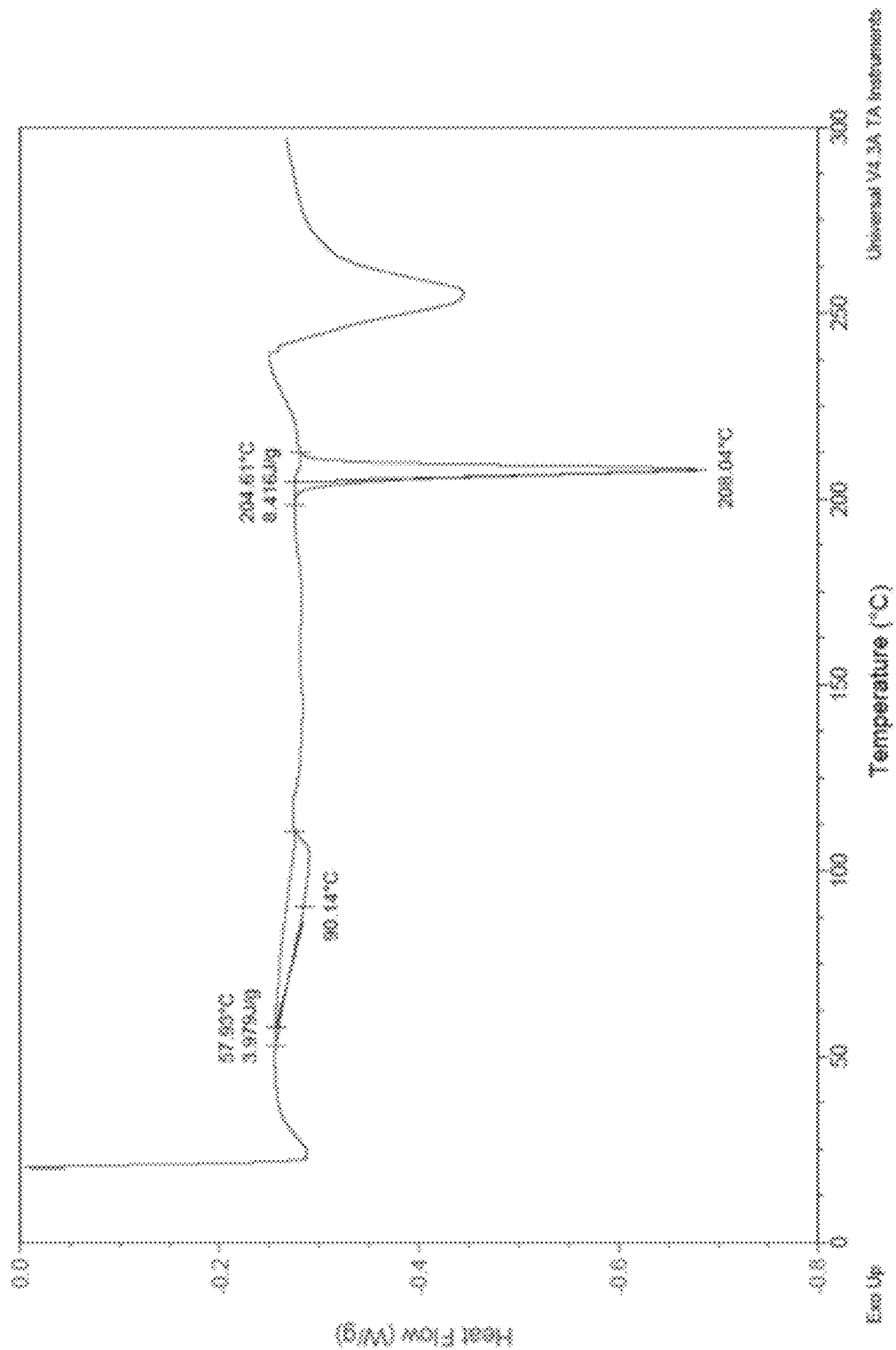
FIG. 3: Representative DSC curve of a sample comprising 10% w/w Pritelivir free base in DDU 4320 silicone elastomer. Entirely similar thermal behavior is observed for Pritelivir free base when incorporated into silicone elastomer at 10% w/w concentration

The DSC traces for Pritelivir alone and in silicone elastomer are presented in FIGS. 2 and 3. Values for onset temperature (° C.), peak temperature (° C.) and enthalpy (ΔH, J/g) for each melting peak are presented in Table 1.

TABLE 1

Thermal parameters for primary crystalline melting transitions observed in DSC traces of various Pritelivir free base and Pritelivir mesylate salt samples. It reflects the dilution effect of the silicone elastomer.

| Sample | Heat flow (ΔH, J/g) | Onset temp (° C.) | Peak temp (° C.) |
|---|---|---|---|
| Pritelivir free base (as supplied) | 56.14 ± 1.49 | 206.18 ± 0.35 | 207.65 ± 0.33 |
| Pritelivir mesylate salt (as supplied) | 77.26 ± 1.21 | 164.52 ± 0.83 | 169.45 ± 0.92 |
| 10% w/w Pritelivir free base in silicone elastomer | 8.41 ± 1.32 | 204.61 ± 1.76 | 207.71 ± 0.75 |
| 10% w/w Pritelivir mesylate salt in silicone elastomer | 8.95 ± 1.32 | 135.79 ± 2.83 | 162.24 ± 2.14 |

Figure 4:
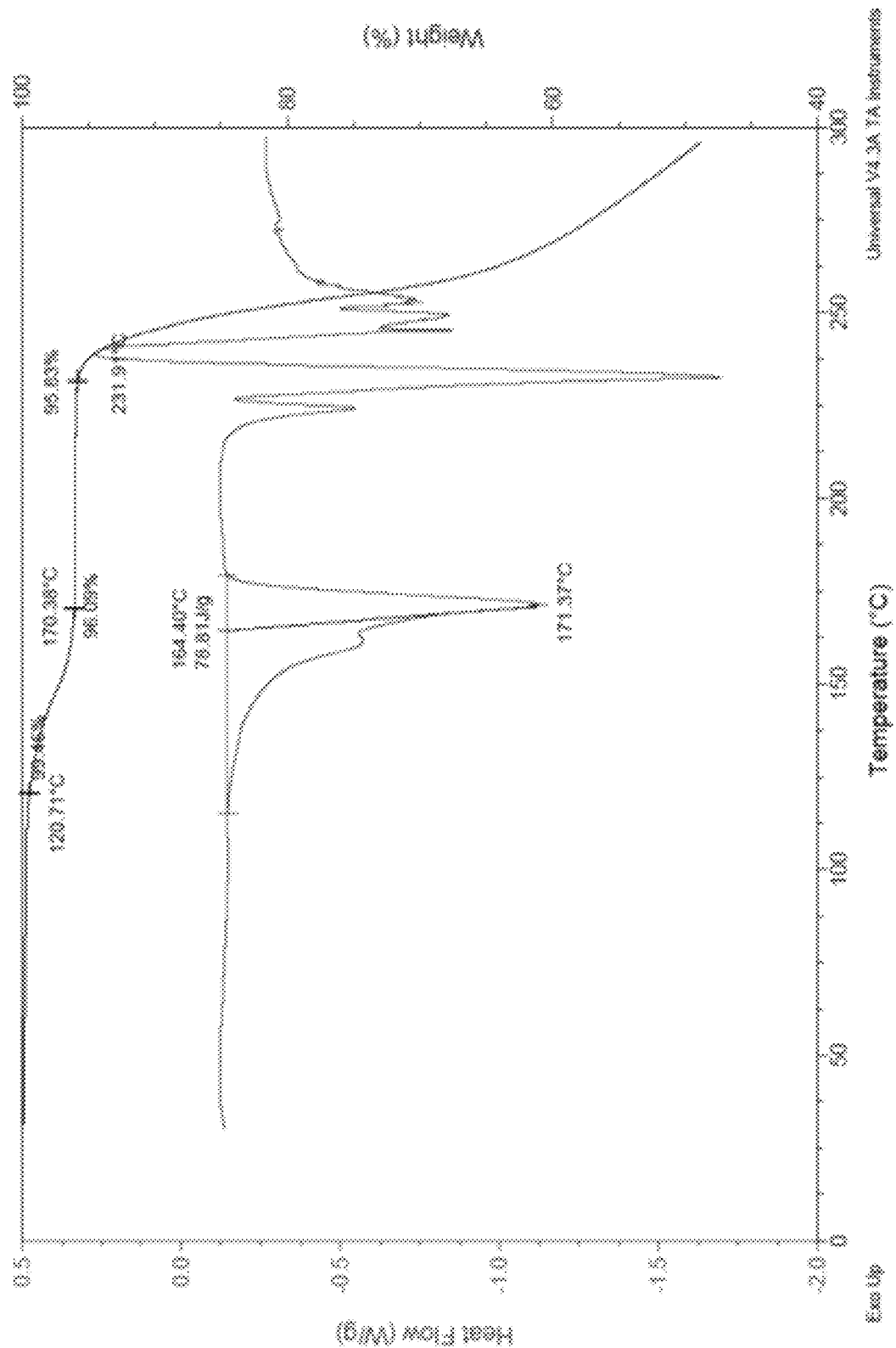
FIG. 4: Representative DSC (Differential Scanning Calorimetry) and TGA (Thermogravimetric analysis) of Pritelivir mesylate salt. The supplied Pritelivir mesylate salt material showed a very broad transition ranging from 110-170° C., with evidence of drug degradation above 210° C. Based on the accompanying TGA data, it appears that this broad transition is due to two processes: solvent loss between 120 and 160° C. followed by melting of the crystalline Pritelivir mesylate salt material at 170° C.
Figure 5:
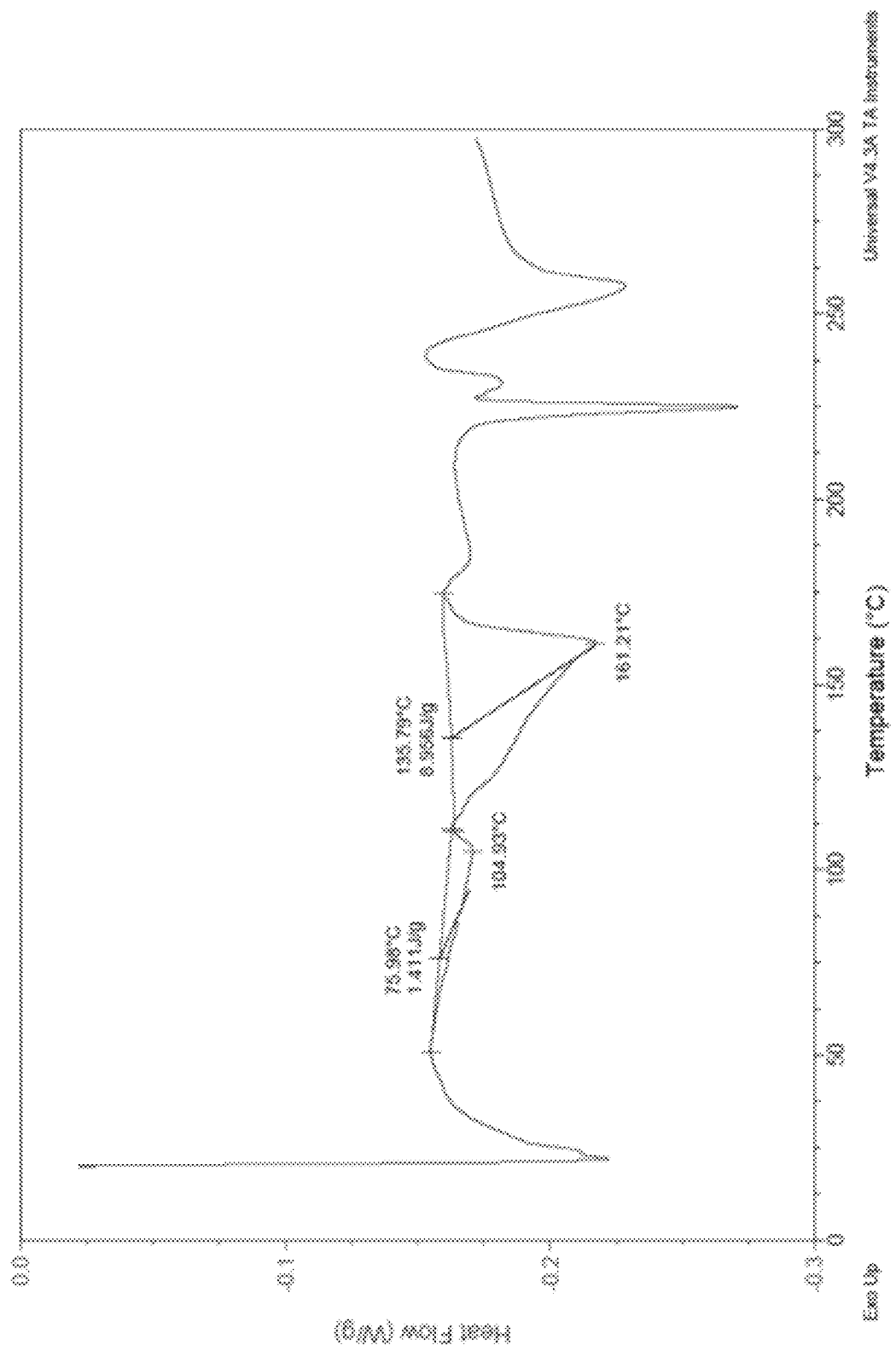
FIG. 5: Representative DSC curve of a sample comprising 10% w/w Pritelivir mesylate salt in DDU 4320 silicone elastomer. Thermal transitions observed for Pritelivir mesylate salt+silicone sample

Pritelivir shows two thermal transitions, a smaller one at 118° C. (attributed to loss of solvent of crystallization and/or a polymorphic transition) and the main crystalline melt at 206° C. (FIG. 2). Thermal decomposition begins around 215° C., as evidenced by the significant mass loss in the TGA curve (FIG. 2). Entirely similar thermal behavior is observed for Pritelivir free base when incorporated into silicone elastomer at 10% w/w concentration (FIG. 3); the primary crystalline melting transition at 205° C. confirms that Pritelivir free base is at least partially present in the dispersed state (i.e. as a crystalline solid) within the ring matrix. The reduced heat flow for the Pritelivir free base+silicone sample compared to Pritelivir free base (as supplied). The supplied Pritelivir mesylate salt material showed a very broad transition ranging from 110-170° C. (FIG. 4), with evidence of drug degradation above 210° C. Based on the accompanying TGA data (FIG. 4), it appears that this broad transition is due to two processes: solvent loss between 120 and 160° C. (note the mass loss in the TGA curve), followed by melting of the crystalline Pritelivir mesylate salt material at 170° C. (no mass loss in TGA curve). The same thermal transitions are mostly also observed in the Pritelivir mesylate salt+silicone sample (FIG. 5); again suggesting that crystalline Pritelivir mesylate salt is present in the silicone elastomer. Further information about the drug materials and the solvents from which they were recrystallized would be required to better interpret these curves. Advantageously, it was realized that incorporation of Pritelivir in the silicone elastomer had no impact on the crystalline nature of the compound. It seems to involve the solubilization of the crystalline drug within the polymer, followed by the permeation of the solubilized drug across the polymer.

In Vitro Release Data

Figure 6:
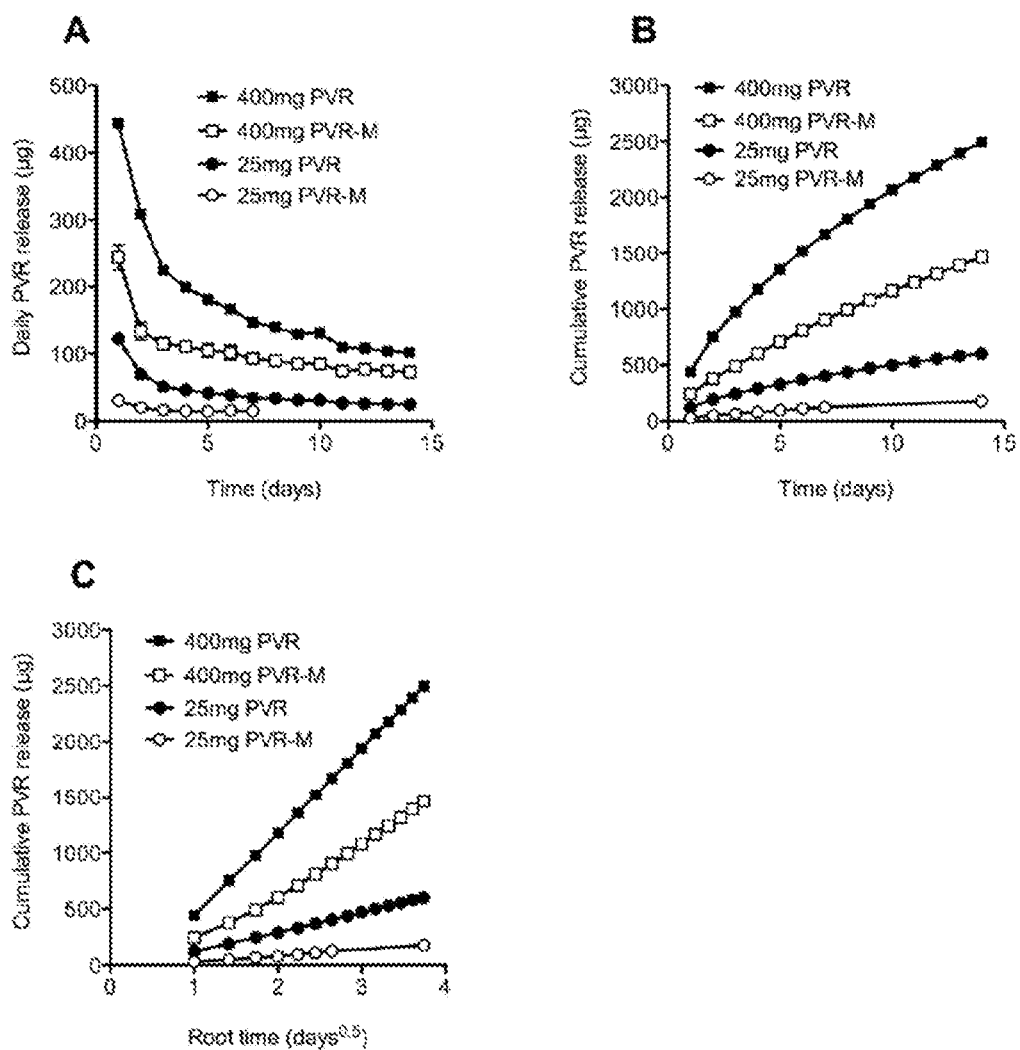
FIG. 6: In vitro release data of both Pritelivir free base (PVR) and Pritelivir mesylate salt (PVR-M) from the matrix-type silicone elastomer vaginal rings (A). Cumulative release vs. time (B) and cumulative release vs. root time (C) plots from the daily release data
Figure 7:
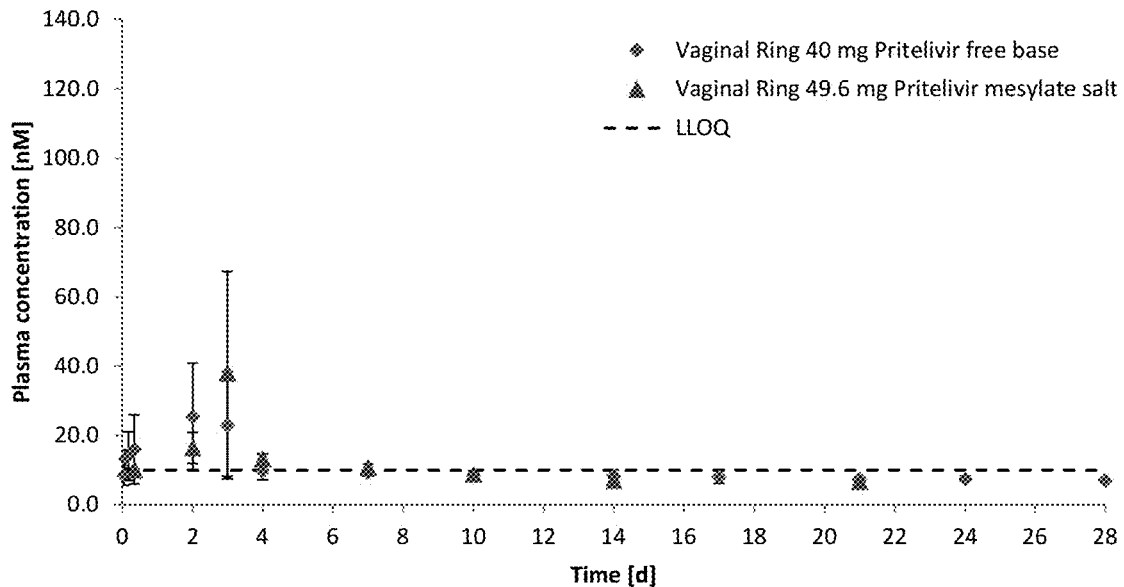
FIG. 7: Mean Pritelivir free base plasma concentration-time profiles after intravaginal administration of a vaginal ring containing 40 mg Pritelivir free base or 49.6 mg Pritelivir mesylate salt to female monkeys (Phase 1)
Figure 8:
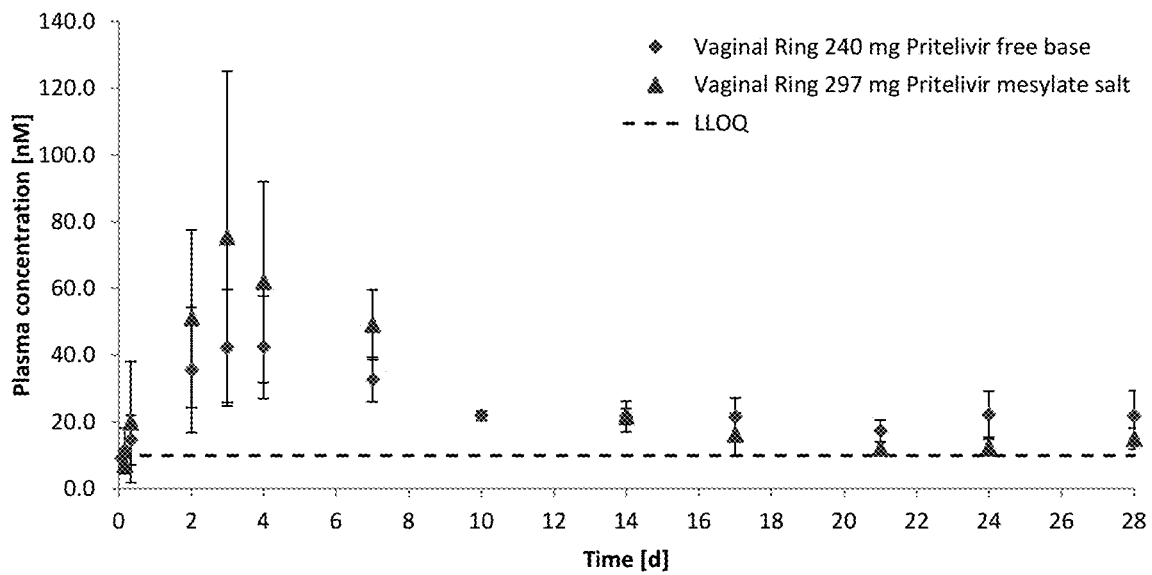
FIG. 8: Mean Pritelivir free base plasma concentration-time profiles after intravaginal administration of a vaginal ring containing 240 mg Pritelivir free base or 297 mg Pritelivir mesylate salt to female monkeys (Phase 2)
Figure 9:
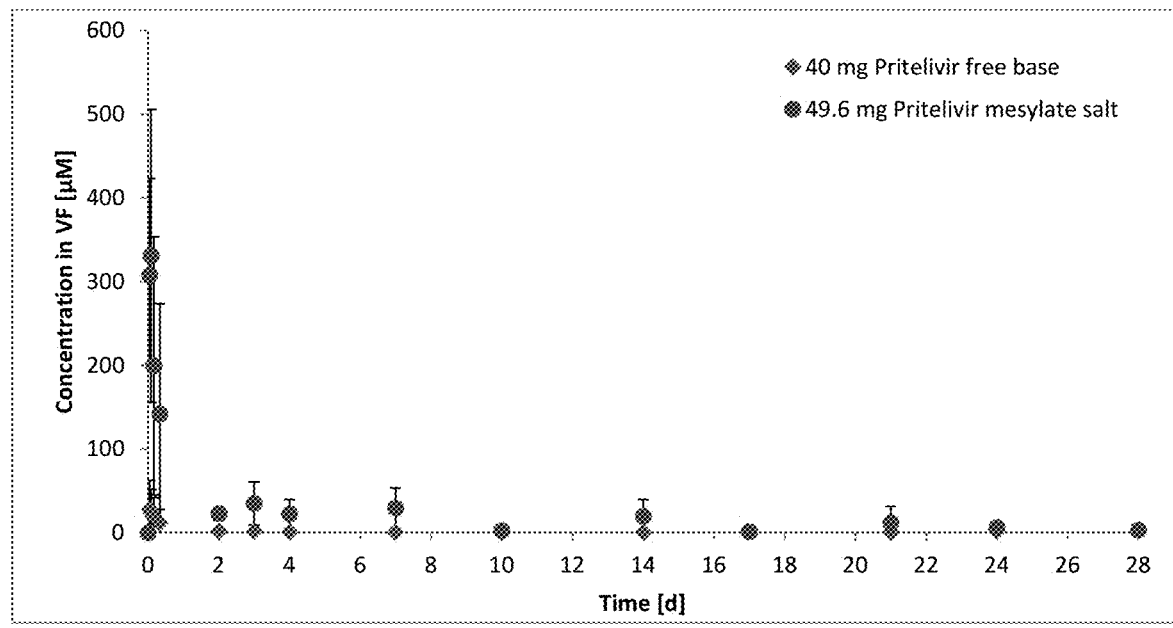
FIG. 9: Mean concentration-time profiles of Pritelivir free base in vaginal fluid after intravaginal administration of a vaginal ring containing 40 mg Pritelivir free base or 49.6 mg Pritelivir mesylate salt to female monkeys (Phase 1)
Figure 10:
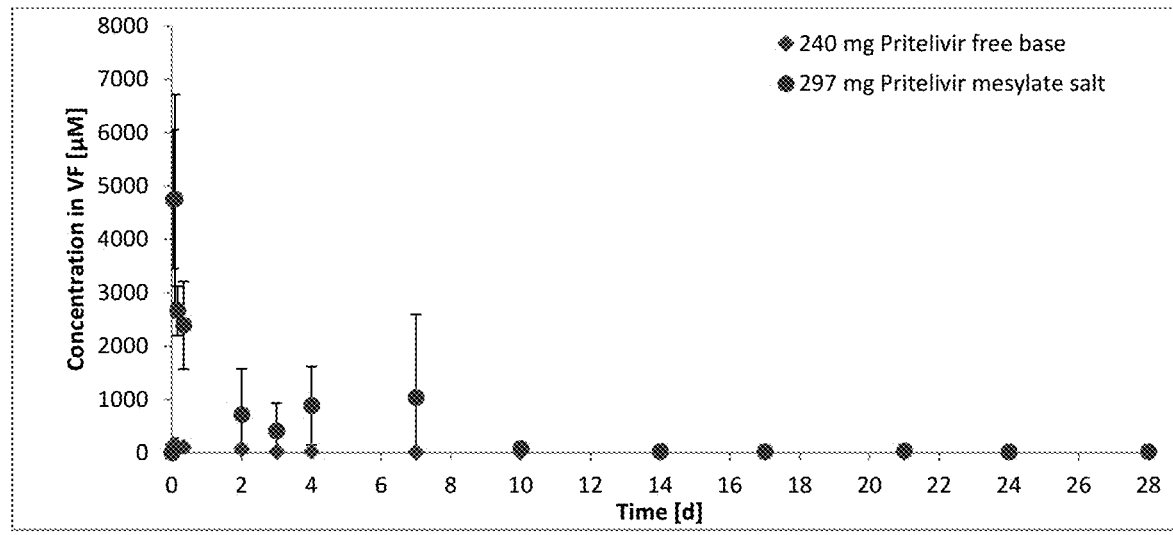
FIG. 10: Mean concentration-time profiles of Pritelivir free base in vaginal fluid after intravaginal administration of a vaginal ring containing 240 mg Pritelivir free base or 297 mg Pritelivir mesylate salt to female monkeys (Phase 2)
Figure 11:
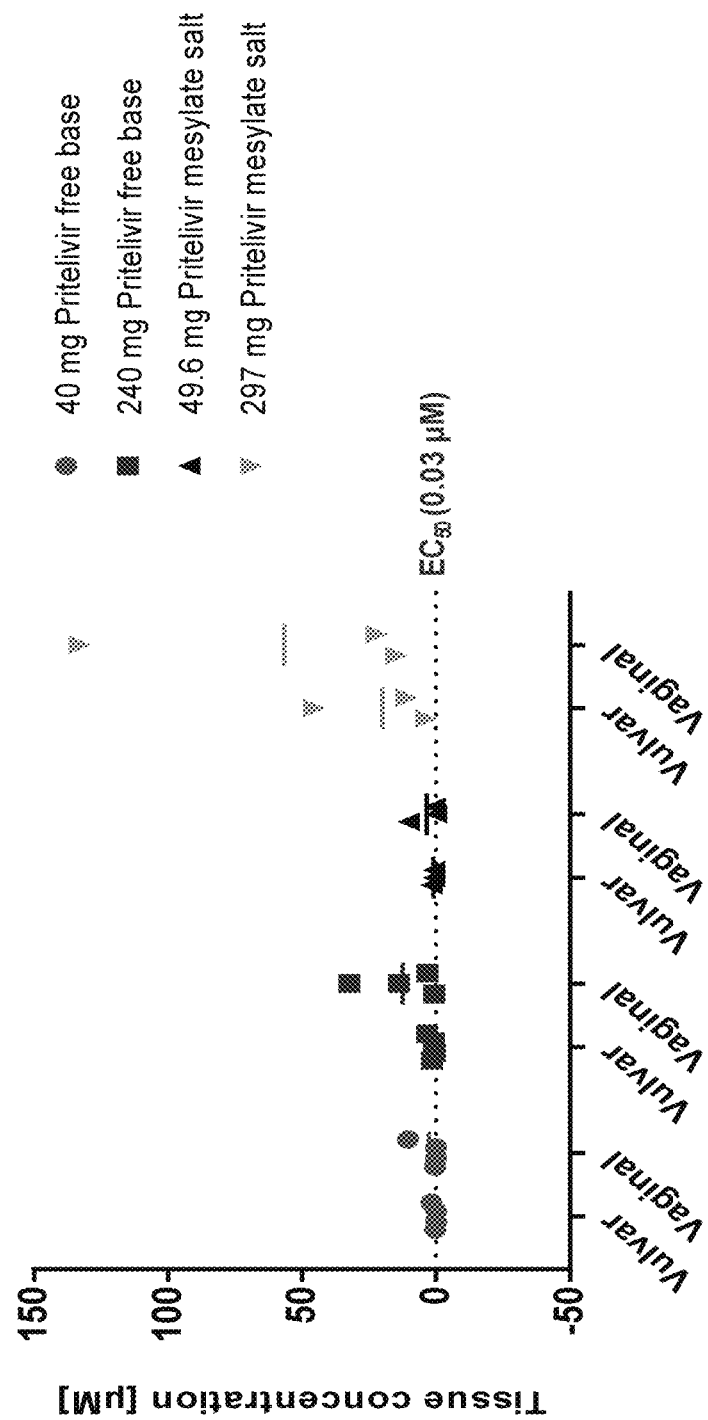
FIG. 11: Comparison tissue concentrations vs. cell culture $EC_{50}$ values for HSV

Both Pritelivir free base and Pritelivir mesylate salt were effectively released from the matrix-type silicone elastomer vaginal rings. The various daily release vs. time profiles (FIG. 6A) showed typical matrix-type behavior, comprising a relatively high day 1 burst attributed to the immediate release properties of the ring followed by steadily decreasing amounts released on subsequent days confirming the potential for a sustained release. Release was highly dependent on both the initial drug loading and the drug type, with the following rank order observed: 400 mg Pritelivir free base>400 mg Pritelivir mesylate salt>25 mg Pritelivir free base >25 mg Pritelivir mesylate salt. Cumulative release vs. time (FIG. 6B) and cumulative release vs. root time (FIG. 6C) plots were constructed from the daily release data. The straight line profiles ($R^2 \geq 0.995$) observed for the cumulative release vs. root time plots (FIG. 6C) indicate that release of Pritelivir free base and Pritelivir mesylate salt from the rings is governed by $t_{1/2}$ kinetics, indicative of a permeation (diffusion) controlled drug release mechanism. Comparative values for release of Pritelivir free base and Pritelivir mesylate salt from the rings are presented in Table 2. Advantageously, using rings as exemplified herein it is possible to achieve sustained release of Pritelivir over at least two weeks.

TABLE 2

Comparative values for release of Pritelivir and Pritelivir mesylate salt from matrix-type vaginal rings

| Ring type | Mean Day 1 release (µg) | Mean Day 14 release (µg) | Cumulative Day 14 release (µg) | Release rate (µg/day) |
| --- | --- | --- | --- | --- |
| Pritelivir free base 25 mg | 122.17 | 24.77 | 604.13 | 177.0 |
| Pritelivir mesylate salt 25 mg | 30.37 | — | 178.79 | 55.5 |
| Pritelivir free base 400 mg | 443.45 | 102.16 | 2,495.52 | 752.5 |
| Pritelivir mesylate salt 400 mg | 243.75 | 73.16 | 1,464.56 | 456.7 |

The results of the study clearly demonstrate the potential for an immediate release of a higher amount on day 1 followed by a controlled sustained release of Pritelivir free base and Pritelivir mesylate salt from silicone elastomer vaginal ring devices. The in vitro release profiles obtained are typical of matrix-type devices where the drug is present above its saturation concentration in the polymer matrix. The solid drug particles provide a reservoir within the ring to replenish the solubilized drug molecules that have been released. This results in 'root time' drug release kinetics, as confirmed by a linear plot of cumulative release vs. root time. Based on the PK data, Pritelivir mesylate salt is clearly the preferred form of the drug for vaginal ring administration. It is assumed that the free base form of Pritelivir is more hydrophobic that the mesylate salt form, which confers surprisingly increased solubility in the silicone elastomer and, in turn, increased permeation rates through the silicone elastomer matrix.

PK Studies in Primates Using Vaginal Rings of Pritelivir Free Base

Study Design

The study was performed in four single dose phases with 28-day sampling period after Phases 1 and 2 (7-day washout period between doses). Vaginal rings were investigated for Pritelivir free base and Pritelivir mesylate salt at two dose levels per formulation. The test items were applied as vaginal ring in Phases 1 and 2 to female monkeys. The study design is below in the Table 3.

TABLE 3

Study design

| Study Phase | Group | Dose level (mg) | Treatment | Formulation | Treatment duration | Observation period |
| --- | --- | --- | --- | --- | --- | --- |
| 1 | 1 | 40 | Pritelivir free base | Vaginal ring | 1 × 28 days | 29 days |
| | 2 | 49.6 | Pritelivir mesylate salt | | | |
| 2 | 1 | 240 | Pritelivir free base | Vaginal ring | 1 × 28 days | 29 days |
| | 2 | 297 | Pritelivir mesylate salt | | | |

Blood, vaginal fluid and tissue was sampled for concentration determination as described in the following sections.

TABLE 4

Treatment groups

| Group | Number of animals | Treatment |
| --- | --- | --- |
| 1 | 4 | Pritelivir free base |
| 2 | 3 | Pritelivir mesylate salt |

Test Item and Formulation

Formulation, test item, drug load and batch numbers are given in table below.

TABLE 5

Test item and formulation

| Study Phase | Test item | Formulation | Drug load (mg) | Ring size (mm) |
| --- | --- | --- | --- | --- |
| 1 | Pritelivir free base | Vaginal ring | 40 | 20 × 4.5 |
| | Pritelivir mesylate salt | Vaginal ring | 49.6 | 20 × 4.5 |
| 2 | Pritelivir free base | Vaginal ring | 240 | 20 × 4.5 |
| | Pritelivir mesylate salt | Vaginal ring | 297 | 20 × 4.5 |

Pharmacokinetic Bleeds

Venous blood samples were taken from all animals at the following times in relation to dosing.

TABLE 6

Blood sampling

| Phase | Sample | Sample times (post-dose) |
| --- | --- | --- |
| 1 | Blood | 0 h (pre-dose), 1 h, 2 h, 4 h, 8 h. Followed by Day 2, 3, 4, 7, 10, 14, 17, 21, 24, 28 |
| 2 | Blood | 0 h (pre-dose), 1 h, 2 h, 4 h, 8 h. Followed by Day 2, 3, 4, 7, 10, 14, 17, 21, 24, 28 |

Blood sample site Femoral site
Blood volume 1.0 mL
Anticoagulant For phase 1 samples, Day 1-3 only, blood was sampled into standard HLS vials containing lithium heparin and 20 μL aqueous phosphoric acid (3.5 molar). Thereafter, blood was collected into tubes containing lithium heparin only. Plasma was obtained from all samples by centrifugation. Samples were appropriately labeled and stored deep frozen (−20° C. or below) until analysis
Total no. of blood samples 350
Vaginal Fluid Sampling Vaginal fluid samples were taken from all animals at the following times in relation to dosing.

TABLE 7

Vaginal fluid sampling

| Phase | Sample | Sample times (post-dose) |
|---|---|---|
| 1 | Vaginal fluid | 0 h (pre-dose), 1 h, 2 h, 4 h, 8 h, followed by Day 2, 3, 4, 7, 10, 14, 17, 21, 24, 28 |
| 2 | Vaginal fluid | 0 h (pre-dose), 1 h, 2 h, 4 h, 8 h, followed by Day 2, 3, 4, 7, 10, 14, 17, 21, 24, 28 |

Sampling was performed by means of Weck-Cel® sponges (held in place in the vagina for 1 minute and then transferred in a container tube immediately after sampling). All Weck-Cel® sponges and container tubes were weighed (to the nearest 1 mg) both before and after sample collection to assess weights of collected fluid samples. Weck-Cel® sponges were not pre-wetted for vaginal fluid sampling. Samples were appropriately labeled and stored in individual 15 mL polypropylene tubes deep frozen (−20° C. or below) until analysis.
Vulval and Vaginal Biopsies Vulval and vaginal biopsies were taken from all animals at the following times in relation to dosing.

TABLE 8

Biopsies

| Phase | Sample | Sample times (post-dose) |
|---|---|---|
| 1 | Vulval and vaginal biopsies | Day 28 |
| 2 | Vulval and vaginal biopsies | Day 28 |

For the sampling biopsies were taken with a suitable biopsy instrument. Biopsy samples were snap frozen on dry ice following collection and stored deep frozen (−20° C. or below) until analysis.
Sample Analysis:

After suitable dilution, plasma and vaginal samples were analyzed on UPLC system Waters Acquity UPLC-HSS PFP column with 1.8 μm particles (100×2.1 mm) by gradient elution using 0.1% formic acid and methanol containing 0.1% formic acid. For detection, a time-of-flight mass spectrometer (Xevo GS-2 QTOF, Waters) was used operating in positive ionization mode (MSe analysis). The samples were analyzed for their content of Pritelivir free base.
Results:

The study was designed to obtain information on the time-course of unchanged test compound concentrations in plasma and vaginal fluid/tissue, following single intravaginal administration of rings to female Cynomolgus monkeys. Objectives of this study were to determine the safety and tolerance of Pritelivir loaded rings, as well as systemic and local exposure (plasma, vaginal fluid and vaginal and vulval tissue, respectively). Local exposures were compared with in vitro efficacy data of Pritelivir to get an idea on initial pharmacokinetic/pharmacodynamic (PK/PD) parameters for vaginal rings, i.e. to assess the potential ability of a Pritelivir loaded ring to suppress viral replication in the target tissue. Table 9 gives an overview on the $EC_{50}$ values of Pritelivir on HSV-1 and HSV-2 Data source: Field, H. J., et al., Baseline sensitivity of HSV-1 and HSV-2 clinical isolates and defined acyclovir-resistant strains to the helicase-primase inhibitor pritelivir. Antiviral Res, 2013. 100(2): p. 297-9. EC50=50% effective concentration.

TABLE 9

Overview on the $EC_{50}$ values of Pritelivir on HSV-1 and HSV-2

| Virus type | $EC_{50}$ (μM) | $EC_{50}$ (μg/L) |
|---|---|---|
| HSV-1 | 0.026 | 10.5 |
| HSV-2 | 0.030 | 12.1 |

Single vaginal doses of Pritelivir inserted as rings with loadings of 40 or 240 mg of Pritelivir free base and 49.6 or 297 mg Pritelivir mesylate, did not result in any adverse findings for clinical signs or body weights. In Phase 1 and 2 of the study, Pritelivir concentrations were determined in plasma, vaginal fluid and tissue up to 28 Days after administration of vaginal rings containing 40 and 240 mg Pritelivir free base (Group 1) or 49.6 and 297 mg Pritelivir mesylate salt (Group 2) to female monkeys. All plasma concentrations of Pritelivir were found to be in the lower nanomolar range (<132 nM or <54 μg/L). Maximal plasma concentrations were reached 2 to 4 days after administration of the vaginal ring. In the following, the concentration decreased until on Day 4 (Phase 1) or on Day 10 (Phase 2) a plateau was reached. From then, the plasma concentration stayed unchanged until Day 14 or longer, e.g., Day 28.

Plasma concentrations showed high inter individual variability with coefficients of variation up to 90%. The plasma concentrations were found to increase dose dependently but sub-proportionally for both test items. Therefore, the systemic exposure of Pritelivir in Cynomolgus monkeys was found to be low after single intravaginal administration of Pritelivir free base or mesylate salt using an matrix type ring. On the other hand, as desired, the tissue concentrations were above $EC_{50}$. Typical concentration vs. time profiles could be observed in vaginal fluid after intravaginal administration of immediate release rings containing Pritelivir free base or Pritelivir mesylate salt. Maximal concentrations were found directly after application of the rings. The concentrations decreased steadily until on Days 4 to 10 a plateau was reached. The concentrations of Pritelivir in vaginal fluid were found to increase more than dose proportional from Phase 1 to Phase 2 for both test items.

Vaginal and vulval biopsies were taken 28 Days after administration of intravaginal rings. As biopsies were not weighed prior extraction, weights were estimated based on data from similar investigations using the same settings for biopsies. From this study minimum, maximum, and mean biopsy weight was used for the calculation. These biopsy weights ranged from 0.7 to 6.3 mg, mean 2.95 mg. For all calculations it was assumed that 1 kg tissue is equal to 1 L water.

In Phase 1, comparable concentrations were found in vaginal and vulval tissue after administration of Pritelivir free base or mesylate salt containing vaginal rings. In Phase 2, the 6-fold higher dose led to 2-fold higher vaginal tissue concentrations for Pritelivir free base and to 10 fold higher vaginal tissue concentrations for Pritelivir mesylate salt. Vulval tissue concentrations increased in a comparable manner.

Generally, concentrations of Pritelivir in plasma, vaginal fluid and tissue were found to be higher after application of rings with Pritelivir mesylate salt when compared to rings with the free base. The free base produced lower plasma concentrations compared to mesylate salt which is an advantage if only low systemic exposure is desired.

TABLE 10

Plasma concentration (in µg/L) of Pritelivir free base after intravaginal administration of a vaginal ring containing 40 mg Pritelivir free base to female monkeys—Phase 1, Group 1

| Time | Concentration of Pritelivir free base (µg/L) | | | | | | |
|---|---|---|---|---|---|---|---|
| (d) | 114 | 116 | 118 | 120 | Mean | SD | % CV |
| 0 | 2.70 $^a$ | nd | nd | nd | nc | nc | nc |
| 0.0417 | 2.44 $^a$ | 4.73 | 3.11 $^a$ | nd | 3.43 $^b$ | 1.17 | 34.3 |
| 0.0833 | nd | 6.03 | 4.53 | nd | 5.28 | 1.06 | 20.1 |
| 0.167 | nd | 6.90 | 7.56 | 2.38 $^a$ | 5.61 $^b$ | 2.82 | 50.3 |
| 0.333 | 2.22 $^a$ | 8.54 | 10.9 | 3.97 | 6.40 $^b$ | 4.00 | 62.5 |
| 2 | 4.07 | 11.6 | 18.3 | 6.75 | 10.2 | 6.23 | 61.2 |
| 3 | 4.80 | 7.29 | 18.4 | 6.30 | 9.20 | 6.22 | 67.6 |
| 4 | 3.21 $^a$ | 3.41 $^a$ | 5.30 | 3.51 $^a$ | 3.86 $^b$ | 0.972 | 25.2 |
| 7 | 3.55 $^a$ | 3.22 $^a$ | 3.86 $^a$ | 4.00 | 3.66 $^b$ | 0.345 | 9.43 |
| 10 | 3.92 $^a$ | 3.02 $^a$ | 3.74 $^a$ | 2.75 $^a$ | 3.36 $^b$ | 0.563 | 16.8 |
| 14 | 2.81 $^a$ | 2.83 $^a$ | 4.32 | 3.29 $^a$ | 3.31 $^b$ | 0.708 | 21.4 |
| 17 | 2.64 $^a$ | 4.08 | 3.48 $^a$ | 2.59 $^a$ | 3.20 $^b$ | 0.716 | 22.4 |
| 21 | nd | 3.00 $^a$ | 3.08 $^a$ | 2.67 $^a$ | 2.91 $^b$ | 0.218 | 7.49 |
| 24 | nd | 3.21 $^a$ | nd | 2.77 $^a$ | 2.99 $^b$ | 0.311 | 10.4 |
| 28 | 2.60 $^a$ | 2.76 $^a$ | 3.00 $^a$ | nd | 2.79 $^b$ | 0.204 | 7.33 | nc: not calculated,
nd not detected
$^a$ below lower limit of quantification (9.93 nM, 4.0 µg/L)
$^b$ calculated with values below lower limit of quantification

TABLE 11

Plasma concentration (in µg/L) of Pritelivir free base after intravaginal administration of a vaginal ring containing 49.6 mg Pritelivir mesylate salt to female monkeys—Phase 1, Group 2

| Time | Concentration of Pritelivir free base (µg/L) | | | | | | |
|---|---|---|---|---|---|---|---|
| (d) | 418 | 422 | 426 | Mean | SD | % CV | |
| 0 | nd | nd | nd | nc | nc | nc | |
| 0.0417 | nd | nd | nd | nc | nc | nc | |
| 0.0833 | 3.10 $^a$ | nd | nd | nc | nc | nc | |
| 0.167 | 2.35 $^a$ | nd | nd | nc | nc | nc | |
| 0.333 | 4.10 | 3.88 $^a$ | nd | 3.99 $^b$ | 0.151 | 3.79 | |
| 2 | 6.00 | 8.59 | 5.13 | 6.58 | 1.80 | 27.4 | |
| 3 | 9.29 | 28.9 | 7.40 | 15.2 | 11.9 | 78.4 | |
| 4 | 5.66 | 4.55 | 5.58 | 5.26 | 0.619 | 11.8 | |
| 7 | 4.71 | 3.84 $^a$ | 4.26 | 4.27 | 0.434 | 10.2 | |
| 10 | 3.40 $^a$ | 3.62 $^a$ | 3.44 $^a$ | 3.49 $^b$ | 0.121 | 3.47 | |
| 14 | nd | 2.99 $^a$ | 2.60 $^a$ | 2.79 $^b$ | 0.277 | 9.93 | |
| 17 | nd | nd | 2.52 $^a$ | nc | nc | nc | |
| 21 | 2.84 $^a$ | 2.47 $^a$ | nd | 2.66 $^b$ | 0.263 | 9.90 | |
| 24 | nd | nd | nd | nc | nc | nc | |
| 28 | 2.43 $^a$ | nd | nd | nc | nc | nc | | nc: not calculated,
nd: not detected,
$^a$ below lower limit of quantification (9.93 nM, 4.0 µg/L)
$^b$ calculated with values below lower limit of quantification

TABLE 12

Plasma concentration (in µg/L) of Pritelivir free base after intravaginal administration of a vaginal ring containing 240 mg Pritelivir free base to female monkeys—Phase 2, Group 1

| Time | Concentration of Pritelivir free base (µg/L) | | | | | | |
|---|---|---|---|---|---|---|---|
| (d) | 114 | 116 | 118 | 120 | Mean | SD | % CV |
| 0 | nd | nd | nd | nd | nc | nc | nc |
| 0.0417 | nd | 2.96 $^a$ | nd | nd | nc | nc | nc |
| 0.0833 | nd | 4.41 | 2.95 $^a$ | nd | 3.68 $^b$ | 1.03 | 28.0 |
| 0.167 | 2.82 $^a$ | 8.45 | 4.56 | 2.49 $^a$ | 4.58 $^b$ | 2.74 | 59.7 |
| 0.333 | 3.78 $^a$ | 10.1 | 5.80 | 3.79 $^a$ | 5.87 $^b$ | 2.98 | 50.8 |
| 2 | 10.1 | 23.0 | 9.89 | nd | 14.3 | 7.53 | 52.6 |
| 3 | 15.6 | 26.8 | 15.2 | 10.2 | 17.0 | 7.01 | 41.3 |
| 4 | 13.9 | 26.0 | 16.1 | 12.2 | 17.0 | 6.18 | 36.3 |
| 7 | 11.8 | 16.4 | 14.2 | 10.3 | 13.1 | 2.68 | 20.4 |
| 10 | 8.27 | 9.46 | 9.04 | 8.43 | 8.80 | 0.553 | 6.28 |
| 14 | 6.33 | 9.48 | 8.33 | 10.6 | 8.70 | 1.84 | 21.1 |
| 17 | 5.58 | 10.8 | 9.84 | 8.41 | 8.67 | 2.29 | 26.4 |
| 21 | 6.02 | 7.78 | 8.37 | 5.71 | 6.97 | 1.30 | 18.7 |
| 24 | 4.96 | 9.71 | 11.3 | 9.86 | 8.97 | 2.77 | 30.9 |
| 28 | 5.57 | 12.7 | 9.32 | 7.55 | 8.79 | 3.03 | 34.5 | nc: not calculated,
nd not detected
$^a$ below lower limit of quantification (9.93 nM, 4.0 µg/L)
$^b$ calculated with values below lower limit of quantification

TABLE 13

Plasma concentration (in μg/L) of Pritelivir free base after intravaginal administration of a vaginal mesylate salt to female monkeys ring containing 297 mg Pritelivir—Phase 2, Group 2

| | Concentration of Pritelivir free base (μg/L) | | | | | |
|---|---|---|---|---|---|---|
| Time (d) | 418 | 422 | 426 | Mean | SD | % CV |
| 0 | nd | nd | nd | nc | nc | nc |
| 0.0417 | nd | nd | nd | nc | nc | nc |
| 0.0833 | nd | nd | 2.62 [a] | nc | nc | nc |
| 0.167 | nd | 5.71 | 3.47 [a] | 4.59 [b] | 1.58 | 34.5 |
| 0.333 | 2.43 [a] | 16.3 | 5.39 | 8.03 [b] | 7.29 | 90.7 |
| 2 | 15.5 | 32.8 | 13.2 | 20.5 | 10.7 | 52.4 |
| 3 | 16.7 | 53.3 | 21.1 | 30.4 | 20.0 | 65.8 |
| 4 | 15.5 | 38.6 | 20.7 | 24.9 | 12.1 | 48.7 |
| 7 | 24.4 | 18.5 | 16.3 | 19.7 | 4.20 | 21.3 |
| 10 | nd | nd | 9.76 | nc | nc | nc |
| 14 | nd | 9.40 | 8.06 | 8.73 | 0.952 | 10.9 |
| 17 | 9.46 | 4.79 | 5.32 | 6.52 | 2.56 | 39.2 |
| 21 | 5.47 | 5.08 | 3.90 [a] | 4.82 [b] | 0.816 | 16.9 |
| 24 | 4.29 | 5.70 | nd | 5.00 | 0.997 | 20.0 |
| 28 | 5.44 | 7.51 | 5.16 | 6.04 | 1.29 | 21.3 | nc: not calculated,
nd: not detected
[a] below lower limit of quantification (9.93 nM, 4.0 μg/L)
[b] calculated with values below lower limit of quantification

TABLE 14

Concentration (in μg/mL) of Pritelivir free base in vaginal fluid after intravaginal administration of a vaginal ring containing 40 mg Pritelivir free base to female monkeys—Phase 1, Group 1

| | Concentration of Pritelivir free base (μg/mL) | | | | | | |
|---|---|---|---|---|---|---|---|
| Time (d) | 114 | 116 | 118 | 120 | Mean | SD | % CV |
| 0 | nd | nd | nd | nd | nc | nc | nc |
| 0.0417 | 7.74 | 3.51 | 31.9 | 1.67 | 11.2 | 14.0 | 125 |
| 0.0833 | 9.21 | 3.19 | 25.6 | 0.547 | 9.65 | 11.3 | 117 |
| 0.167 | 4.76 | 2.25 | 21.6 | 1.39 | 7.50 | 9.51 | 127 |
| 0.333 | 2.38 | 0.0880 | 14.4 | 1.85 | 4.68 | 6.56 | 140 |
| 2 | 0.306 | 0.0172 | 2.81 | 0.0645 | 0.800 | 1.35 | 168 |
| 3 | 0.565 | 0.191 | 1.15 | 0.725 | 0.657 | 0.396 | 60.3 |
| 4 | 0.937 | 0.101 | 0.346 | 0.151 | 0.384 | 0.384 | 100 |
| 7 | 0.583 | 0.0748 | 0.239 | 0.0885 | 0.246 | 0.236 | 96.0 |
| 10 | 0.191 | 0.0143 | 0.274 | 0.575 | 0.264 | 0.234 | 88.7 |
| 14 | 0.103 | 0.0817 | 0.127 | 0.201 | 0.128 | 0.0521 | 40.6 |
| 17 | 0.137 | 0.0348 | 0.467 | 0.159 | 0.199 | 0.186 | 93.5 |
| 21 | 0.0000 | 0.241 | 0.434 | 0.272 | 0.237 | 0.179 | 75.6 |
| 24 | 0.481 | 0.0000 | 1.14 | 0.828 | 0.612 | 0.489 | 40.4 |
| 28 | 0.712 | 0.0000 | 1.66 | 0.185 | 0.639 | 0.744 | 87.7 | nc: not calculated,
nd not detected

TABLE 15

Concentration (in μg/mL) of Pritelivir free base in vaginal fluid after intravaginal administration of a vaginal ring containing 49.6 mg Pritelivir mesylate salt to female monkeys—Phase 1, Group 2

| | Concentration of Pritelivir free base (μg/mL) | | | | | |
|---|---|---|---|---|---|---|
| Time (d) | 418 | 422 | 426 | Mean | SD | % CV |
| 0 | nd | nd | nd | nc | nc | nc |
| 0.0417 | 103 | 177 | 92.0 | 124 | 46.3 | 37.4 |
| 0.0833 | 201 | 138 | 60.5 | 133 | 70.4 | 52.9 |
| 0.167 | 110 | 122 | 8.96 | 80.2 | 62.1 | 77.3 |
| 0.333 | 112 | 53.1 | 6.24 | 57.1 | 53.0 | 92.8 |
| 2 | 12.7 | 6.42 | 8.48 | 9.20 | 3.20 | 34.8 |
| 3 | 18.4 | 21.6 | 2.24 | 14.1 | 10.4 | 73.7 |
| 4 | 16.3 | 2.43 | 8.43 | 9.05 | 6.95 | 76.8 |
| 7 | 23.0 | 4.98 | 7.52 | 11.8 | 9.73 | 82.3 |
| 10 | 1.31 | 0.189 | 1.41 | 0.969 | 0.677 | 69.9 |
| 14 | 2.18 | 0.0000 | 13.7 | 5.28 | 7.33 | 139 |
| 17 | 1.13 | 0.105 | 0.638 | 0.623 | 0.511 | 82.0 |
| 21 | 0.455 | 0.334 | 14.0 | 4.91 | 7.83 | 159 |
| 24 | 4.11 | 0.732 | 2.50 | 2.45 | 1.69 | 69.1 |
| 28 | 1.64 | 2.00 | 0.184 | 1.27 | 0.961 | 75.4 | nc: not calculated,
nd: not detected

TABLE 16

Concentration (in μg/mL) of Pritelivir free base in vaginal fluid after intravaginal administration of a vaginal ring containing 240 mg Pritelivir free base to female monkeys—Phase 2, Group 1

| | Concentration of Pritelivir free base (μg/mL) | | | | | | |
|---|---|---|---|---|---|---|---|
| Time (d) | 114 | 116 | 118 | 120 | Mean | SD | % CV |
| 0 | nd | nd | nd | nd | nc | nc | nc |
| 0.0417 | 3.51 | 60.7 | 126 | 41.7 | 58.0 | 51.3 | nc |
| 0.0833 | 26.1 | 22.1 | 63.8 | 1.36 | 28.3 | 26.0 | 88.4 |
| 0.167 | 34.6 | 29.5 | 48.5 | 40.1 | 38.2 | 8.15 | 91.8 |
| 0.333 | 38.8 | 50.0 | 73.2 | 14.2 | 44.1 | 24.5 | 21.3 |
| 2 | 19.2 | 16.5 | 67.3 | 11.2 | 28.5 | 26.1 | 55.6 |
| 3 | 14.0 | 2.29 | 11.2 | 10.8 | 9.57 | 5.06 | 91.3 |
| 4 | 7.04 | 4.99 | 21.9 | 5.27 | 9.80 | 8.13 | 52.9 |
| 7 | 3.19 | 1.68 | 6.84 | 1.04 | 3.19 | 2.60 | 82.9 |
| 10 | 1.89 | 1.77 | 12.9 | 4.23 | 5.21 | 5.28 | 81.5 |
| 14 | 0.912 | 1.30 | 5.37 | 3.32 | 2.72 | 2.06 | 101 |
| 17 | 3.96 | 1.13 | 9.97 | 1.93 | 4.25 | 4.00 | 75.5 |
| 21 | 4.21 | 1.17 | 9.02 | 0.254 | 3.66 | 3.95 | 94.1 |
| 24 | 2.77 | 5.48 | 7.89 | 2.36 | 4.63 | 2.58 | 108 |
| 28 | 4.04 | 2.19 | 6.29 | 3.50 | 4.00 | 1.71 | 55.7 | nc: not calculated,
nd: not detected

TABLE 17

Concentration (in μg/mL) of Pritelivir free base in vaginal fluid after intravaginal administration of a vaginal ring containing 297 mg Pritelivir mesylate salt to female monkeys—Phase 2, Group 2

| | Concentration of Pritelivir free base (μg/mL) | | | | | |
|---|---|---|---|---|---|---|
| Time (d) | 418 | 422 | 426 | Mean | SD | % CV |
| 0 | nd | nd | nd | nc | nc | nc |
| 0.0417 | 1318 | 2117 | 2304 | 1913 | 524 | 27.4 |
| 0.0833 | 2352 | 2387 | 1006 | 1915 | 787 | 41.1 |
| 0.167 | 1114 | 868 | 1232 | 1071 | 186 | 17.3 |
| 0.333 | 702 | 1333 | 850 | 962 | 330 | 34.3 |
| 2 | 26.5 | 680 | 156 | 287 | 346 | 120 |
| 3 | 406 | 74.0 | 17.9 | 166 | 210 | 126 |
| 4 | 537 | 14.8 | 513 | 355 | 295 | 83.1 |
| 7 | 105 | 1140 | 6.15 | 417 | 628 | 151 |
| 10 | 69.4 | 23.9 | 9.32 | 34.2 | 31.3 | 91.6 |
| 14 | 15.9 | 3.72 | 15.0 | 11.6 | 6.80 | 58.8 |
| 17 | 8.87 | 8.41 | 10.3 | 9.21 | 1.01 | 11.0 |
| 21 | 23.0 | 17.4 | 8.96 | 16.4 | 7.05 | 42.9 |
| 24 | 10.2 | 7.32 | 1.87 | 6.47 | 4.24 | 65.6 |
| 28 | 10.9 | 3.00 | 11.2 | 8.37 | 4.65 | 55.6 | nc: not calculated,
nd: not detected

TABLE 18

Vaginal tissue concentration (in μg/g) of Pritelivir free base after intravaginal administration of a vaginal ring containing Pritelivir free base or Pritelivir mesylate salt to female monkeys—Phase 1 and 2

| Phase | Test Item | Dose | Animal no. | Concentration (μg/g) | | | % CV |
|---|---|---|---|---|---|---|---|
| | | | | Min | Max | Mean | |
| 1 | Pritelivir free base | 40 mg | 114 | 1.98 | 17.9 | 4.24 | 132 |
| | | | 116 | <2.0 | <2.0 | <2.0 | |
| | | | 118 | 0.0694 | 0.625 | 0.148 | |
| | | | 120 | <2.0 | <2.0 | <2.0 | |
| | Pritelivir mesylate salt | 49.6 mg | 418 | 0.103 | 0.929 | 0.220 | 127 |
| | | | 422 | 1.94 | 17.5 | 4.15 | |
| | | | 426 | <2.0 | <2.0 | <2.0 | |
| 2 | Pritelivir free base | 240 mg | 114 | 0.135 | 1.21 | 0.288 | 115 |
| | | | 116 | 6.10 | 54.9 | 13.0 | |
| | | | 118 | 0.599 | 5.39 | 1.28 | |
| | | | 120 | 2.62 | 23.6 | 5.59 | |
| | Pritelivir mesylate salt | 297 mg | 418 | 2.80 | 25.2 | 5.98 | 117 |
| | | | 422 | 4.18 | 37.6 | 8.92 | |
| | | | 426 | 25.1 | 226 | 53.6 | |

<2.0, <0.005: below lower limit of quantification (0.005 μM, 2.0 μg/L)
Remark: calculations assuming 1 L = 1 kg

TABLE 19

Vulval tissue concentration (in μg/g) of Pritelivir free base after intravaginal administration of a vaginal ring containing Pritelivir free base or Pritelivir mesylate salt to female monkeys—Phase 1 and 2

| Phase | Test Item | Dose | Animal no. | Concentration (μg/g) | | | % CV |
|---|---|---|---|---|---|---|---|
| | | | | Min | Max | Mean | |
| 1 | Pritelivir free base | 40 mg | 114 | 0.370 | 3.33 | 0.791 | 121 |
| | | | 116 | <2.0 | <2.0 | <2.0 | |
| | | | 118 | 0.0149 | 0.134 | 0.0318 | |
| | | | 120 | 0.0825 | 0.742 | 0.176 | |
| | Pritelivir mesylate salt | 49.6 mg | 418 | 0.150 | 1.35 | 0.320 | 54.2 |
| | | | 422 | 0.340 | 3.06 | 0.726 | |
| | | | 426 | 0.137 | 1.24 | 0.293 | |
| 2 | Pritelivir free base | 240 mg | 114 | 0.293 | 2.63 | 0.625 | 80.8 |
| | | | 116 | 0.0944 | 0.849 | 0.202 | |
| | | | 118 | 0.642 | 5.78 | 1.37 | |
| | | | 120 | 0.171 | 1.54 | 0.364 | |
| | Pritelivir mesylate salt | 297 mg | 418 | 0.697 | 6.27 | 1.49 | 111 |
| | | | 422 | 2.08 | 18.7 | 4.44 | |
| | | | 426 | 8.58 | 77.2 | 18.3 | |

<2.0, <0.005: below lower limit of quantification (0.005 μM, 2.0 μg/L)
Remark: calculations assuming 1 L = 1 kg

EMBODIMENTS OF THE INVENTION

1. A device for the intravaginal administration of Pritelivir.

2. The device according to embodiment 1, wherein Pritelivir is selected from the group comprising the free base of Pritelivir and Pritelivir mesylate salt.

3. The device according to embodiment 1 comprising a composition comprising the free base of Pritelivir and/or the Pritelivir mesylate salt.

4. The device according to any one of embodiments 1 to 3, wherein the device comprises a biostable and biocompatible polymer matrix.

5. The device according to any one of embodiments 1 to 4, wherein the device comprises a biostable and biocompatible polymer matrix comprising a silicone elastomer.

6. The device according to any one of embodiments 1 to 5, wherein the device is an intravaginal ring.

7. The device according to any one of embodiments 1 to 6, wherein the device is suitable for immediate release of Pritelivir.

8. The device according to any one of embodiments 1 to 6, wherein the device is suitable for sustained release of Pritelivir.

9. The device according to any one of embodiments 1 to 6, wherein the device is suitable for controlled release of Pritelivir.

10. The device according to any one of embodiments 1 to 6, wherein the device is suitable for immediate and sustained release of Pritelivir.

11. The device according to any one of embodiments 1 to 6, wherein the device is suitable for immediate and controlled sustained release of Pritelivir.

12. The device according to any one of embodiments 1 to 11, wherein the device comprises Pritelivir in a total amount of at least 25 mg, at least 30 mg, at least 40 mg, at least 50 mg, at least 75 mg, at least 100 mg, at least 150 mg, at least 200 mg, at least 225 mg, at least 230 mg, or at least 240 mg.

13. The device according to any one of embodiments 1 to 7, and 10 to 12, wherein the device is suitable for immediate release of Pritelivir, and wherein anti-herpes simplex virus effective concentration $EC_{50}$ of ≥0.03 μM is measured after 24 hours post-administration of the device in vaginal fluid.

14. The device according to any one of embodiments 1 to 8 and 10 to 13, wherein the device is suitable for immediate and sustained release of Pritelivir, and wherein anti-herpes simplex virus effective concentration $EC_{50}$ of ≥0.03 μM is measured at least for 7 days post-administration of the device in vaginal fluid and/or vaginal and/or vulvar tissue.

15. The device according to any one of embodiments 1 to 14, wherein the Pritelivir is present in an amount selected from the group of ranges comprising 0.01% w/w to 40.0% w/w, 0.1% w/w to 20.0% w/w, 0.25% w/w-10.0% w/w, 0.25% w/w to 7.5% w/w, and 0.25% w/w to 1.0% w/w.

16. The device according to any one of embodiments 1 to 15, wherein the Pritelivir is present in an amount selected from the range of 0.3 to 5.5% w/w.

17. The device according to any one of embodiments 1 to 16, wherein the concentration of Pritelivir in a plasma sample of an individual receiving said device in a period of 1 to 28 days post-administration of said device is ≤100 nM≤50 nM, ≤30 nM, ≤20 nM, or ≤10 nM.

18. The device according to any one of embodiments 1 to 17, wherein the plasma concentration of Pritelivir in a period of 1 to 28 days post-administration of the device is ≤50 nM, ≤30 nM, ≤20 nM, or ≤10 nM.

19. The device according to any one of embodiments 1 to 18, wherein the concentration of Pritelivir in vaginal fluid or in vaginal or vulvar tissue in a period of 1 to 28 days post-administration of the device is in a range of 0.1 to 3,000 μM in a period from day 2 to day 14 post-administration.

20. The device according to any one of embodiments 1 to 19, characterized in that a daily dose of 0.1 to 500.0 μg is released from the ring in a period from day 2 to day 14 post-administration of the device to a patient, and/or wherein a daily dose of 0.1 to 50.0 μg is released from the ring in a period from day 14 to day 28 post-administration of the device.

21. The device according to any one of embodiments 1 to 20, characterized in that a concentration of 0.001 to 750 μM of Pritelivir is present in vaginal tissue 28 days and/or about 2.0 to 250 μg Pritelivir per gram vaginal tissue post-administration of the device.

22. The device according to any one of embodiments 1 to 21, wherein said device comprises at least one additional active ingredient.

23. The device according to any one of embodiments 1 to 22, wherein said device comprises at least one additional active ingredient, selected from the group of antiviral agents, anti-inflammatory agents, analgesics, anesthetics, antibiotics, hormones.

24. The device according to any one of embodiments 1 to 23, wherein said device comprises at least one additional antiviral active ingredient, wherein said ingredient is selected from the group comprising HSV antiviral agent, an HIV antiviral agent, or both HSV and HIV antiviral agents.

25. The device according to any one of embodiments 22 to 24, wherein said HSV antiviral agents are selected from a group comprising valacyclovir, acyclovir, famciclovir, penciclovir, ganciclovir, glycyrrhizic acid and derivatives thereof, *Sambucus nigra*, propolis, L-lysine, docosanol, valganciclovir, or a salt, solvate or a combination thereof.

26. The device according to any one of embodiments 22 to 24, wherein said HIV antiviral agents are selected from a group comprising tenofovir, emtricitabine, lamivudine, efavirenz, raltegravir, dolutegravir, maraviroc, rilpirivine, or a salt, solvate or a combination thereof.

27. The device according to any one of embodiments 1 to 26, wherein the said device releases Pritelivir in vitro in an amount of 10.0 to 500.0 µg on day 1 and/or 10.0 to 125 µg after 14 days in a 1:1 Vol/Vol solution of isopropanol:$H_2O$ when determined by HPLC.

28. The device according to any one of embodiments 1 to 27, wherein the said device releases Pritelivir in vitro at a rate of 0.1 to 500.0 µg/day in 1:1 Vol/Vol solution of isopropanol:$H_2O$ when determined by HPLC.

29. The device according to any of the preceding embodiments for use in a method of treatment and/or prevention of a genital herpes virus infection.

30. The device according to any of the preceding claims for use in a method of treatment and/or prevention of a genital herpes virus transmission.

31. The device for use in a method of treatment and/or prevention of a genital herpes virus infection according to embodiments 29 and 30, wherein the genital herpes virus is selected from the order of simplex viruses.

32. The device according for use in a method of treatment and/or prevention of a genital herpes virus infection according to embodiments 29 to 31, wherein said simplex virus is selected from Herpes Simplex Virus 1 and Herpes Simplex Virus 2.

33. The device according for use in a method of treatment and/or prevention of a genital herpes virus infection according to any one of embodiments 29 to 32, wherein viral shedding and genital lesions and recurrences are suppressed.

34. The device according for use in a method of treatment and/or prevention of a genital herpes virus infection according to any one of embodiments 29 to 33, wherein the device is for administration to patients in need thereof selected from the group of women diagnosed with a genital herpes virus infection, women that are HSV seropositive, women suspected to have a genital herpes virus infection, women suffering from or suspected to suffer from a bacterial or fungal infection of the genital tract or from a non-herpetic virus infection of the genital tract, women wishing to get pregnant, pregnant women, women having sexual intercourse with men diagnosed as suffering from or suspected to suffer from an infection of the genital tract, particularly an infection with herpes simplex virus, women that are recipients of an organ transplant or expecting to receive an organ transplant, immunosuppressed women, women having sexual intercourse with men that are that are recipients of an organ transplant or expecting to receive an organ transplant, women having sexual intercourse with immunosuppressed men, women having children aged 0 to 18 years that are recipients of an organ transplant or expecting to receive an organ transplant or that are immunosuppressed, women suffering from an HIV or HPV infection.

35. The device according for use in a method of treatment and/or prevention of a genital herpes virus infection according to any one of embodiments 29 to claim 34, wherein a first device is administered and replaced by at least one further device administered after 14 to 28 days, and wherein each subsequent device is administered after 14 to 28 days to replace the previously administered device.

36. A method of treatment or prevention/suppression of an infection with genital herpes caused by herpes simplex virus Type 1 or Type 2, or prevention/suppression of transmission of a genital herpes caused by herpes simplex virus Type 1 or Type 2, or prevention of acquisition of a genital herpes caused by herpes simplex virus Type 1 or Type 2, comprising administering to a subject in need thereof the device according to any of the preceding embodiments.

37. A medicinal kit comprising at least one device according to any of the preceding embodiments in a suitable container and instructions for use in a suitable packing.

38. A process for the manufacture of a device according to any one of the preceding embodiments comprising the steps of:
 a) Mixing a biostable and biocompatible polymer and Pritelivir;
 b) Injection-molding the mixture obtained in step a).

The invention claimed is:

1. A device for the intravaginal administration of the free base of Pritelivir, the Pritelivir mesylate salt or a combination of the free base of Pritelivir and the Pritelivir mesylate salt, wherein the device comprises a composition comprising the Pritelivir mesylate salt or a composition comprising a combination of the free base of Pritelivir and the Pritelivir mesylate salt.

2. The device according to claim 1, wherein the device comprises a biostable and biocompatible polymer matrix.

3. The device according to claim 2, wherein the biostable and biocompatible polymer matrix comprises a silicone elastomer.

4. The device according to claim 1, wherein the device comprises a biostable and biocompatible polymer matrix comprising a silicone elastomer.

5. The device according to claim 4, wherein the device is an intravaginal ring.

6. The device according to claim 1, wherein the device is an intravaginal ring.

7. The device according to claim 6, wherein the device is suitable for immediate release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

8. The device according to claim 6, wherein the device is suitable for sustained release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

9. The device according to claim 6, wherein the device is suitable for controlled release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

10. The device according to claim 6, wherein the device is suitable for immediate and sustained release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

11. The device according to claim 6, wherein the device is suitable for immediate and controlled sustained release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

12. The device according to claim 1, wherein the device is suitable for immediate release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

13. The device according to claim 1, wherein the device is suitable for sustained release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

14. The device according to claim 1, wherein the device is suitable for controlled release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

15. The device according to claim 1, wherein the device is suitable for immediate and sustained release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt.

16. The device according to claim 1, wherein the device is suitable for immediate and controlled sustained release of the free base of Pritelivir, the Pritelivir mesylate salt or a combination of the free base of Pritelivir and the Pritelivir mesylate salt from a composition comprising the Pritelivir mesylate salt or a composition comprising a combination of the free base of Pritelivir and the Pritelivir mesylate salt.

17. The device according to claim 16, wherein the composition comprising the Pritelivir mesylate salt or a composition comprising a combination of the free base of Pritelivir and the Pritelivir mesylate salt provides an equivalent amount of the free base of Pritelivir which totals at least 25 mg, at least 30 mg, at least 40 mg, at least 50 mg, at least 75 mg, at least 100 mg, at least 150 mg, at least 200 mg, at least 225 mg, at least 230 mg, or at least 240 mg.

18. The device according to claim 1, wherein the composition comprising the Pritelivir mesylate salt or a composition comprising a combination of the free base of Pritelivir and the Pritelivir mesylate salt provides an equivalent amount of the free base of Pritelivir which totals at least 25 mg, at least 30 mg, at least 40 mg, at least 50 mg, at least 75 mg, at least 100 mg, at least 150 mg, at least 200 mg, at least 225 mg, at least 230 mg, or at least 240 mg.

19. The device according to claim 1, wherein the device is suitable for immediate release of the free base of Pritelivir, the Pritelivir mesylate salt or a combination of the free base of Pritelivir and the Pritelivir mesylate salt, from a composition comprising the Pritelivir mesylate salt or a composition comprising a combination of the free base of Pritelivir and the Pritelivir mesylate salt, and wherein anti-herpes simplex virus effective concentration EC50 of >0.03 µM is measured after 24 hours post-administration of the device in vaginal fluid.

\* \* \* \* \*